(12) United States Patent
Harris

(10) Patent No.: US 8,057,083 B2
(45) Date of Patent: Nov. 15, 2011

(54) FIBRE BUNDLE CONFOCAL ENDOMICROSCOPE

(75) Inventor: Martin Russell Harris, Windsor (AU)

(73) Assignee: Optiscan Pty, Ltd., Notting Hill (AU)

( * ) Notice: Subject to any disclaimer, the term of this patent is extended or adjusted under 35 U.S.C. 154(b) by 433 days.

(21) Appl. No.: 11/795,421

(22) PCT Filed: Jan. 20, 2006

(86) PCT No.: PCT/AU2006/000069
§ 371 (c)(1),
(2), (4) Date: Aug. 28, 2007

(87) PCT Pub. No.: WO2006/076772
PCT Pub. Date: Jul. 27, 2006

(65) Prior Publication Data
US 2008/0137363 A1    Jun. 12, 2008

(30) Foreign Application Priority Data
Jan. 21, 2005   (AU) ................. 2005900259

(51) Int. Cl.
*F21V 8/00* (2006.01)
(52) U.S. Cl. ......... 362/574; 362/553; 362/556; 362/575
(58) Field of Classification Search .......... 362/574, 362/553, 554, 575, 556; 600/178, 181, 182; 359/368, 385; 385/33, 48
See application file for complete search history.

(56) References Cited

U.S. PATENT DOCUMENTS

| | | | | |
|---|---|---|---|---|
| 4,682,029 A * | 7/1987 | Diepeveen et al. | ........... | 250/330 |
| 5,528,045 A * | 6/1996 | Hoffman et al. | ........... | 250/458.1 |
| 5,926,592 A * | 7/1999 | Harris et al. | ........... | 385/33 |
| 6,836,597 B2 * | 12/2004 | Chan | ........... | 385/39 |

FOREIGN PATENT DOCUMENTS

| | | |
|---|---|---|
| WO | WO 91/15792 | 10/1991 |
| WO | WO 94/10595 | 5/1994 |
| WO | WO 03/090613 | 11/2003 |
| WO | WO 03/090613 A1 * | 11/2003 |

* cited by examiner

*Primary Examiner* — Sharon Payne
(74) *Attorney, Agent, or Firm* — Patterson Thuente Christensen Pedersen, P.A.

(57) ABSTRACT

A fiber bundle confocal microscope or endoscope (200), comprising a light source (142) for providing a beam of light (160), a coherent fiber bundle of optical fibers (152), a scanner (202) for receiving the beam and scanning the beam over a proximal end of the bundle (162), so that the beam is launched into a plurality of the fibers sequentially, a plurality of the fibers thereby acting sequentially as an at least one delivery fiber (204), a spatial filter (172), and a photodetector (174) operatively associated with the spatial filter to receive return light from one or more of the fibers. The return light from the delivery fiber is excluded from the photodetector by the spatial filter.

18 Claims, 19 Drawing Sheets

FIBRE BUNDLE CONFOCAL ENDOMICROSCOPE

RELATED APPLICATION

This application claims priority to PCT Application No. PCT/AU2006/000069 filed Jan. 20, 2006, and Australian Application No. 2005900259 filed Jan. 21, 2005, the disclosures of which are hereby incorporated by reference in their entireties.

FIELD OF THE INVENTION

The present invention relates to the field of fiber bundle confocal microscopy and endoscopy, and is of particular but by no means exclusive application in endomicroscopy.

BACKGROUND OF THE INVENTION

Image transfer (coherent) optical fiber bundles have been used to inspect the interior cavities of the body for the diagnosis and monitoring of disease. They can also be used as the image optical transfer path component in confocal systems. Unlike in the case of a vibrating single fiber, the cores in the tips of the bundle are not acting as confocal pinholes; this function is provided by a spatial filter or filters, such as in the form of a pinhole, associated with a scanning mechanism outside the subject.

Existing fiber bundle confocal systems generally scan a single laser point in a raster pattern on the surface of the tips of the fibers of the bundle, using X and Y mirrors to effect the scan, although the same principle also works with line-scan, Nipkow disc or other confocal systems.

FIG. 1 is a schematic view of a basic point-scanning laser confocal system 10 of the background art that employs a coherent fiber bundle as an image transfer element. A beam of light 12 from a laser 14 shines on a beam-splitter 16 and a portion 18 of the light 12 is reflected onto an x-y beam-scanner 20. The scanned beam 22 passes through lens 24 to focus to a spot at the entry of core 26 of a respective optic fiber 28 on the polished proximal face 30 of the coherent fiber bundle 32. The light passes down the fiber 28 to the distal end 34 of fiber 28, from which it emerges as a divergent beam 36 that is completely captured by collimating lens 38. This light proceeds as a parallel, collimated beam 40 to an objective lens 42 that brings it to a focus as a diffraction-limited Gaussian waist 44 within the specimen under examination. If a portion of the specimen within that waist region 44 fluoresces or reflects light then that light travels in the reverse direction (via the same path as the excitation light described above) until it reaches beam-splitter 16. Some of this return light exits the beam-splitter 16 as a beam 46 and is focussed by lens 48 to a diffraction limited Gaussian waist 50 bounded by a spatial filter pinhole 52. The light passing through pinhole 52 impinges on a photodetector (such as a PMT) 54 and generates an electrical signal. This signal is fed into a bitmap in a frame-store 56 and is displayed as a point 58 on the screen of a monitor 60.

A scan generator 62 shifts the x-y beam-scanner 20 and hence beam 22 to a new path 64 so that the light travels through a different fiber 66 (at a considerable distance from the first fiber 28), illuminating another portion of the specimen at a different Gaussian waist 68; this portion is displayed on the screen of monitor 60 at 70. The scan generator 62 also provides an output signal to frame-store 56 so that frame-store 56 can assign the correct instantaneous x and y coordinates to the signal received from photodetector 54. Ultimately system 10 builds up a final image 72.

Coherent bundles have the major advantage in endoscopy of eliminating any need for a mechanical scanning mechanism within the subject. However, as each fiber core is discrete and separate, with six neighbouring fibers, there is the risk of undersampling and a hexagonal honeycomb overlay is imposed on the ultimate images.

Further, the fiber bundle loses a considerable amount of light, which is further compounded by the undersampling, for the following reasons. If the fiber cores were touching and were arranged in a square array, that is, centred on a rectangular grid, then from information theory principles the figure for linear undersampling in one row should be 2.3 (the Nyquist number) and the a real undersampling $2.3^2$. In fact the cores in a fiber bundle are hexagonally close packed, so that the next row of fibers is actually 0.7071 diameters below the first row and the figure for undersampling in this direction is 2.3×0.7071=1.61. This makes the average figure for (linear) undersampling slightly less than 2 (or in terms of areal undersampling, somewhat less than 4).

In this example, if a purely geometric analysis is performed, approximately 9% of the light falling on a hexagonally close packed array of circular fibers will pass into the gaps between the fibers. However the fiber cores are separated by the combined cladding of each pair of adjacent fibers and, as described above, this cladding must be of finite thickness to avoid photon tunneling between the cores; such tunneling would otherwise cause optical crosstalk and image degradation. Photons which arrive at the bundle tip in the cladding region are either absorbed by the cladding within a short distance of the tip or are diverted at such a high angle that they are not guided but traverse across the cores to be absorbed at the outer sheath of the bundle. The cladding does not act as a funnel at the tip for the photons, there has to be a "dead zone" in between the cores to stop tunneling.

Apart from causing light loss, this dead-zone also adds to the undersampling; if the laser input beam were carefully matched to a single fiber in a polished tip of a bundle, it is possible to launch over 80% of light to reach the other end of the bundle. The loss is from tip reflections (~8%), Raleigh scattering, and glass absorption.

If the laser beam is defocused to cover several cores, the transmission typically drops to ~20%. This implies by geometric arguments that the dead zone makes up around 75% of the polished tip area. It follows from this that the cores are effectively separated by a full core diameter of cladding and that the linear undersampling figure is approximately double that for cores in close contact. This number will vary slightly with wavelength, bundle type and beam profile. (As a separate issue the dead area also implies that 75% of the scanning acquisition time will not be used, unless the laser spot is scanned along the lines of cores only.)

FIG. 2 is another schematic view of the background art system 10 of FIG. 1, and illustrates under-sampling resulting from the discrete nature of the separate fibers of the bundle 32 when using the illustrated system. For the purposes of explanation the illumination of the specimen is shown as being carried out (successively) by two adjacent fibers 80a and 80b. The respective Gaussian waists 82a and 82b of the light focussed by the objective lens 42 do not overlap. Hence respective portions of the specimen in Gaussian waists 82a and 82b will be imaged as 84a and 84b on the screen of monitor 60, but a portion of the specimen at 86 between Gaussian waists 82a and 82b will not be imaged. This constitutes a high degree of under-sampling.

The most obvious feature of fiber bundle images is the reticulated or hexagonal pattern overlay. In some approaches this is removed by acquiring a (highly oversampled) image of the bundle tip and using it to subtract pixel for pixel from the raw images. The pattern can also be removed by deliberately blurring the image or by filter transform processing. These methods improve viewability but at the cost of some information.

To obtain full resolution with maximum light efficiency, however, it would be necessary to sample at points between the discrete core positions shown. The vibrating tip fiber system is able to sample at as many points as desired during the scan.

Another existing approach avoids undersampling and attains full resolution potential as follows. If the numerical aperture (NA) of the fibers in the bundle is matched to the back NA of the lens (as is done in a scanning tip system), then the optical efficiency is at a maximum but the image is undersampled. Pixel intensity values for points building up the image can only be obtained from one fiber and then from the next adjacent fiber core, but the Nyquist sampling criterion requires measurements from points in between. The finite cladding thickness needed to prevent evanescent coupling and cross-talk (i.e. light leakage) between adjacent fibers further separates the cores, and the total linear undersampling value is then close to 4. Full optical resolution can be obtained by synchronized mechanical movement ("dithering") of the fiber bundle tips at both ends by a few core diameters in X and Y during image acquisition. This allows intensities of pixels to be obtained between the static core positions and eliminate the hexagonal honeycomb overlay pattern of the close packed fibers. From the discussion above it can be seen that it would be necessary to integrate approximately 16 scans (i.e. the square of the linear undersampling figure) to produce one image with full resolution. Mechanical scanning at the distal tip can be effected with piezo actuator elements of the type used to shift a CCD or CMOS chip in a digital camera, to increase resolution or to act as image stabilizers. At the proximal (i.e. laser source) end of the bundle an identical piezo-mechanical system can be used, or an equivalent result could be achieved in the computer by a shift in the frame register of the image.

FIG. 3 is a schematic view illustrating this background art technique for removing under-sampling by simultaneously dithering proximal and distal tips of the fiber bundle, and thereby obtaining samples at intermediate positions. The system 90 of FIG. 3 is generally like laser confocal system 10 of FIGS. 1 and 2, and like reference numerals have been used to identify like features. In addition, system 90 includes mini x actuators 92a, 92b (at the proximal and distal tips of the fiber bundle 32 respectively) controlled by controller 94 and mini y actuators 96a, 96b (at the proximal and distal tips of the fiber bundle 32 respectively) controlled by controller 98; these mini x and y actuators 92a, 92b, 96a, 96b simultaneously dither the proximal and distal tips of fiber bundle 32. When combined with the effects of beam-scanner 20, imagining can thereby be performed at intermediate positions.

Another existing method to obtain full resolution is to deliberately mismatch the fiber NA and the lens back-NA. A fiber bundle with smaller, high NA cores or a longer focal length collimating lens is used, so that the excitation light overfills the focussing lens. With this approach, the Airy discs projected within the specimen from adjacent fibers overlap, thus allowing the specimen fluorescence to be sampled at intermediate positions and satisfy the Nyquist criterion. The confocal light returning from each of these points (which are acting as sources) in the specimen projects its own Airy disc onto several fiber cores, most of which overlap from one pixel to the next. The return confocal pinhole at the proximal end must then accept light from this cluster of cores.

FIGS. 4A and 5 are schematic views of a background art system 100 in which the distal lens is highly overfilled. System 100 can give full resolution by allowing sampling at the Nyquist criterion intervals. In FIG. 4A the optical system is generally identical with that of FIG. 1, and like reference numerals have been used to identify like features. However, system 100 includes a collimating lens 102 of greater focal length than that of FIG. 1. This means that the distal lens assembly (comprising collimating lens 102 and objective lens 42) is further from the distal tip of fiber bundle 32, and the Gaussian waists 104 (which are identical in size with those in FIG. 2) now overlap and give proper sampling within the specimen being observed.

For clarity the illumination of the specimen is shown in FIG. 4A as being carried out by two adjacent fiber cores 106a, 106b in the fiber bundle 32. This does not occur simultaneously.

FIG. 4B is an enlarged view of region 108 of FIG. 4A. As is more apparent in this detail, Gaussian waist 110a resulting from the light transmitted along core 106a overlaps Gaussian waist 110b resulting from the light transmitted along core 106b.

FIG. 5 depicts the same optical arrangement as that of FIG. 4A but showing the return light rays from one point in the specimen. The Airy disc of the return light now falls on a cluster fiber tips 112 of seven fibers 114 at the distal end of the bundle 32. (For clarity, only the three fiber tips in the central plane of the cluster are shown.) The pinhole 52 is enlarged to allow the light emitted from the seven proximal cores 116 to pass to the photodetector 54. This gives full resolution but with a worse signal/noise ratio owing to the wasting of excitation light from the overfilling and the loss of return light in the cladding.

FIG. 6 is a schematic view of another background art system 120, similar to system 10 of FIG. 1 and like reference numerals have been used to identify like features. However, distal lenses (cf. lenses 38 and 42 in FIG. 1) are not used; instead, the distal face 122 (which is polished) of the fiber bundle 32 directly touches the tissue 124 to be imaged. Excitation light passes along a single fiber 28 of the bundle 32 and light from components 126 of the tissue 124 close to the distal face 122 returns back along the same fiber 28, passes through the beam-splitter 16 and pinhole 52 to a single photodetector 54, and is imaged at 128 on the screen of monitor 60. Similarly (though not simultaneously), excitation light transmitted by another fiber 66 illuminates another portion 130 of the tissue 124, and is ultimately imaged at 132 on the screen of monitor 60. A complete, contact microscopy image is eventually generated. The signal to noise ratio of the image, however, is degraded by Raman, Raleigh and Fresnel noise, and is affected by dirt on the polished bundle face 122.

However, in order to obtain full optical resolution using available bundles and the above techniques that employ distal tip lenses, over 95% of the laser excitation light is discarded. The mismatch also means that, in the return direction, the cladding absorbs about 75% of the return confocal light as the mode fields no longer match. In order to compensate for the poor light budget, the input power must be increased, but this increases the level of Raman scattering within the bundle and hence degrades the S/N ratio.

Hence, both the signal is reduced and the higher laser power generates correspondingly more noise within the fiber cores. Indeed, if full optical resolution with a bundle system is desired in existing systems, the laser power required to achieve the same level of fluorescent return signal will be 50 times greater. That is, the optical efficiency will be much less than 5% (i.e. $\frac{1}{16}$th of 25%) of that of a single fiber tip scanner.

This degrades the S/N ratio in three ways:
1) Statistical noise due to photon arrival variation is worse if laser power is limited by medical safety requirement;
2) Noise from Raman scattering in the fiber core is very much worse; and
3) Fluorescence saturates (and fluorescent return tails off) while Raman generation increases linearly with laser intensity. The 25% confocal return figure pushes the fluorophore more into the saturated region.

Of these the noise from Raman scattering is generally the most significant. Spectral filtering can be used to remove some of this noise, but Raman lines from glass are broad because of the range of bond energies in the liquid glass. Methods of removing Raman interference do exist. For example, Raman noise is generated instantaneously so can be removed from the fluorescent signal using a FLIM system, but this requires pulsed lasers and time gated detectors.

SUMMARY OF THE INVENTION

According to the present invention, therefore, there is provided a fiber bundle confocal microscope or endoscope, comprising:
a light source for providing a beam of light;
a coherent fiber bundle of optical fibers;
a scanner for receiving the beam and scanning the beam over a proximal end of the bundle (as, for example, a line or spot), so that the beam is launched into a plurality of the fibers sequentially, a plurality of the fibers thereby acting sequentially as an at least one delivery fiber;
a spatial filter; and
a photodetector operatively associated with the spatial filter to receive return light from one or more of the fibers;
wherein return light from the delivery fiber is excluded from the photodetector by the spatial filter.

Thus, the fiber bundle confocal microscope or endoscope of this embodiment takes advantage of the fact that all the excitation light at any instant is delivered by one or more "delivery" fibers, whilst the confocal return light is carried by the delivery fiber or fibers and—principally—the six immediately surrounding fibers. Almost all the noise returning to the photodetector, however, is generated in the core of the delivery fiber or fibers. Occluding the return and other light emitted towards the photodetector by the delivery fiber or fibers reduces the intensity of that light by less than half, but reduces the noise—especially from Raman scattering—dramatically.

It is then possible, by means—for example—of an annular spatial filter provided in a detector pinhole plane—to block the region corresponding to the core of the delivery fiber, and thus eliminate almost all of the Raman noise while losing only a fraction of the confocal return signal.

Also, the substantial dead zone between the cores is, in this invention, advantageous in that it allows one to ensure that light is not launched into two cores simultaneously.

The microscope or endoscope may comprise a further photodetector for receiving return light transmitted by the delivery fiber.

The microscope or endoscope may comprise an endomicrosope, and in other aspects the invention provides an endoscope for internal or external use.

The spatial filter may comprise a mechanical filter with an occlusion to intercept return light from the delivery fiber. In one embodiment the light source is a laser source and the occlusion a spot; in another embodiment the light source is a line source and the occlusion is linear.

The spatial filter may comprise one or more optical elements (such as a mirror, a lens, an array of mirrors or an array of lenses) arranged to direct return light other than return light from the delivery fiber to the photodetector.

In some embodiments, a plurality of the fibers act simultaneously as delivery fibers, and return light from the delivery fibers is excluded from the photodetector by the spatial filter The spatial filter may comprise an entry aperture of the photodetector.

The microscope or endoscope may include a plurality of photodetectors operatively associated with the spatial filter to receive return light from one or more of the fibers.

The microscope or endoscope may include one or more optical transmitters for transmitting return light to the photodetector. The spatial filter may comprise an entry of the one or more optical transmitters.

The microscope or endoscope may include a beam splitter that also acts as the spatial filter.

The scanner may comprise a pair of scannable mirrors. The microscope or endoscope may further comprise a second scanner for scanning an image formed by the microscope or endoscope and operable to scan synchronously with the scanner. The scanner may comprise a stationary mirror and a scannable mirror, and the second scanner comprises a stationary mirror and a scannable mirror.

The microscope or endoscope may further comprise a double sided mirror with a first side comprising the scannable mirror of the scanner and a second side comprising the scannable mirror of the second scanner.

In one particular embodiment, the invention provides a fiber bundle confocal microscope or endoscope, comprising:
a laser source for providing a beam of coherent light;
a coherent fiber bundle of optical fibers;
a scanner for receiving the beam and scanning the beam over a proximal end of the bundle, so that the beam is launched into a plurality of the fibers sequentially, each of the fibers thereby acting sequentially as a delivery fiber;
a spatial filter defining an aperture;
a photodetector operatively associated with the spatial filter; and
an occlusion operatively associated with the spatial filter to intercept at least a portion of light emitted by the delivery fiber at the proximal end of the bundle.

In one embodiment, the spatial filter includes the occlusion, wherein the occlusion is located at the centre of the aperture defined by the spatial filter. In a particular embodiment, the spatial filter defines an annular aperture, wherein the occlusion comprises the centre of the annulus.

The central portion of the annulus can be supported by a "spider", or it could be supported by a glass sheet. An occlusion in the form of a variable central occluding stop could also be advantageous and this feature is achievable by the use of a Travis stop which can be expanded or contracted to adjust the amount of central blocking.

The invention also provides a method of providing confocal microscopy or endoscopy, comprising excluding from a photodetector return light from one or more delivery fibers in a fiber bundle confocal microscope or endoscope.

The photodetector may comprise a plurality of separate photodetectors.

The method may include excluding from the photodetector return light from one or more delivery fibers by means of a spatial filter operatively associated with the photodetector.

In one embodiment, the method comprises occluding the return light from the delivery fiber in a fiber bundle confocal microscope or endoscope.

BRIEF DESCRIPTION OF THE DRAWING

In order that the invention may be more clearly ascertained, embodiments will now be described, by way of example, with reference to the accompanying drawing, in which.

DETAILED DESCRIPTION

Figure 8:
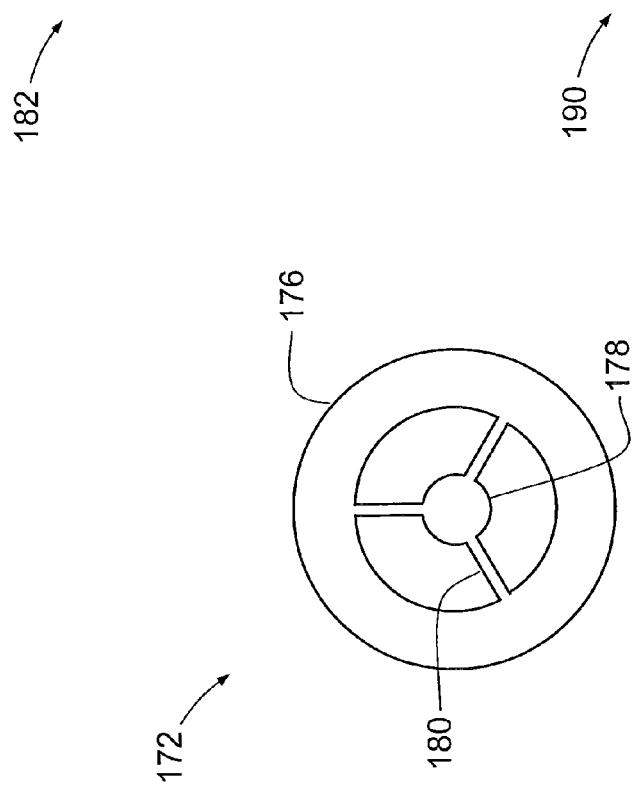
FIG. 8 is a schematic view of the annular aperture of the fiber bundle confocal endomicroscope of FIG. 7.

A fiber bundle confocal endomicroscope according to an embodiment of the invention is shown generally at 140 in FIG. 8. The endomicroscope 140 comprises a TEM00 laser source 142, a beam splitter 144, x and y scanning mirrors 146, 148, a field lens 150, a fiber optic bundle 152, a collimating lens 154 and a focussing lens 156 (located for focussing light onto or into a sample 158).

In use, the laser source 142 emits a beam of light 160 which passes through beam splitter 144 onto the x and y scanning mirrors 146, 148 and to the field lens 150. The field lens 150 focuses the beam onto the proximal polished face 162 of fiber optic bundle 152.

Field lens 150 is chosen so as to project a Gaussian waist spot into the core of a single fiber of the bundle 152 at any one time. As will be appreciated by those skilled in the art, the identity of the single fiber changes as the beam is scanned over the proximal face 162 of the bundle 152. This fiber is thus referred to as the delivery fiber, but the identity of the delivery fiber changes as scanning moves the beam to the next fiber (whether adjacent or otherwise) sequentially.

The beam then travels along the core of the delivery fiber until it reaches the distal end of the delivery fiber at the distal end 164 of the bundle 152. The light emerges from the distal end of the delivery fiber and falls on collimating lens 154. A fibers of the fiber bundle 152 have small, high NA cores, so that the excitation light overfills the collimating lens. The solid angle of the emitted cone of light 166 thus considerably exceeds the solid angle of acceptance of the collimating lens 154.

Owing to this over filling, the spots from adjacent fiber cores when focussed in the sample 158 overlap considerably. This allows a sampling frequency which satisfies the Nyquist criterion and provides full resolution of structures in the tissue which can be chosen or adjusted to admit only the "confocal" rays.

Endomicroscope 140 also includes, for collecting return light, a condensing lens 170, a spatial filter with a central occlusion, in the form of annular aperture or spatial filter 172, and a photodetector in the form of photomultiplier 174. Although light is delivered to the sample along a single delivery fiber, it returns along multiple fibers centred on the delivery fiber. Typically the bulk of the return signal is transmitted by seven fibers: the delivery fiber and the six fibers immediately adjacent to the delivery fiber, hence arranged in a honeycomb pattern. The return light is imaged on the aperture defined by the annular aperture 172, so the light emitted by the delivery fiber—being central in that image—is occluded by the central portion of the annulus. Most of the noise, particularly from Raman scattering, originates in the delivery fiber, so noise is thereby blocked by the central portion of the annular aperture 172. Although some signal is also thus lost, a great improvement in signal to noise ratio is produced.

FIG. 8 is a schematic view of the annular aperture 172. The annular aperture 172 includes outer ring 176 and central, occluding portion 178. The central portion 178 is supported on ring 176 by three legs 180.

The occluding portion need not be in the precise plane of the aperture. Indeed, in some applications it may be more convenient if it is displaced slightly either optically before or after the aperture or other spatial filter. This is possible because of the finite distance between the core of the delivery and the cores of the adjacent fibers so, even when the return light is somewhat out of focus (such as just before the aperture) there will be little if any overlap between the light returned by the delivery fiber and that returned by the adjacent fibers.

Figure 9:
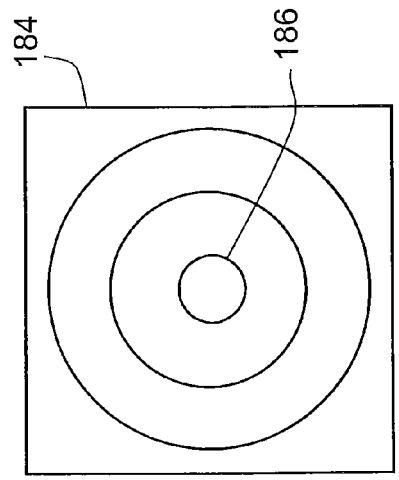
FIG. 9 is a schematic view of an annular aperture according to another embodiment of the present invention.

FIG. 9 is a schematic view of an alternative annular aperture 182. The annular aperture 182 is mounted on glass 184, so that the central, occluding portion 186 can be attached to the glass 184. This obviates the need for supporting legs (like legs 180 of FIG. 8).

Figure 10:
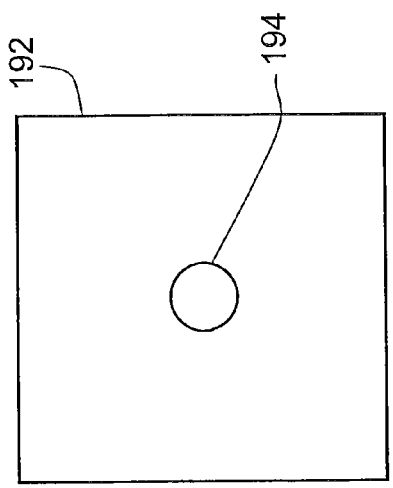
FIG. 10 is a schematic view of an aperture according to another embodiment of the present invention.

FIG. 10 is a schematic view of a still further alternative aperture 190. This aperture 190 is similar to aperture 182 of FIG. 9 and includes supporting glass 192 and central, occluding portion 194. However, it omits an outer ring (cf. ring 176 of FIG. 8). Hence, this aperture will either have much reduced depth resolution, as any spatial filtering will be provided by whatever supporting structure is employed to support aperture 190, or would be used in conjunction with a conventional spatial filter, possibly optically immediately before that conventional spatial filter.

In an alternative embodiment, an occlusion can be provided in the form of a variable central occluding stop, such as a Travis stop, which can be expanded or contracted to adjust the amount of central blocking.

Figure 1:
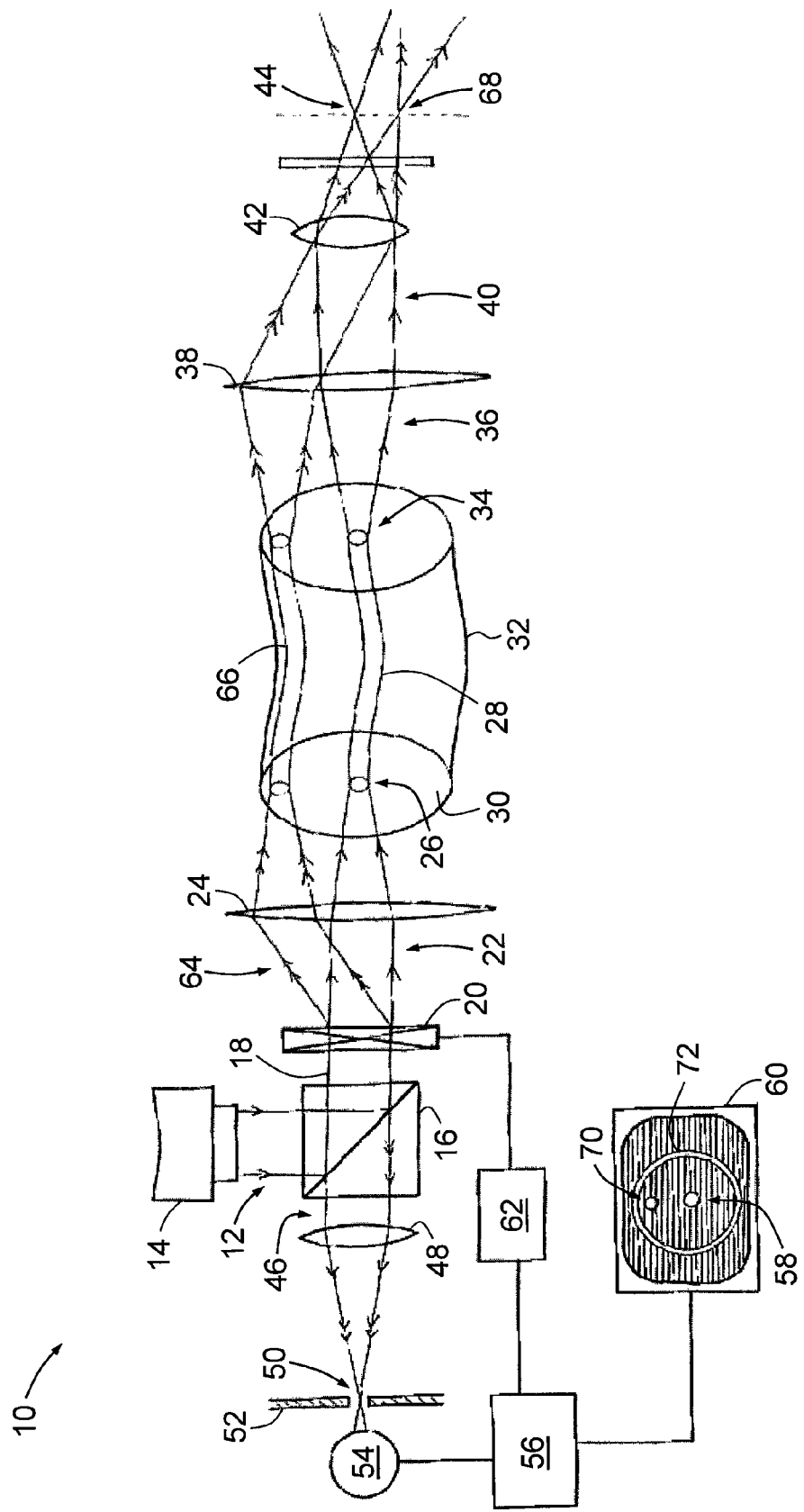
FIG. 1 is a schematic view of a basic point-scanning laser confocal system of the background art.
Figure 2:
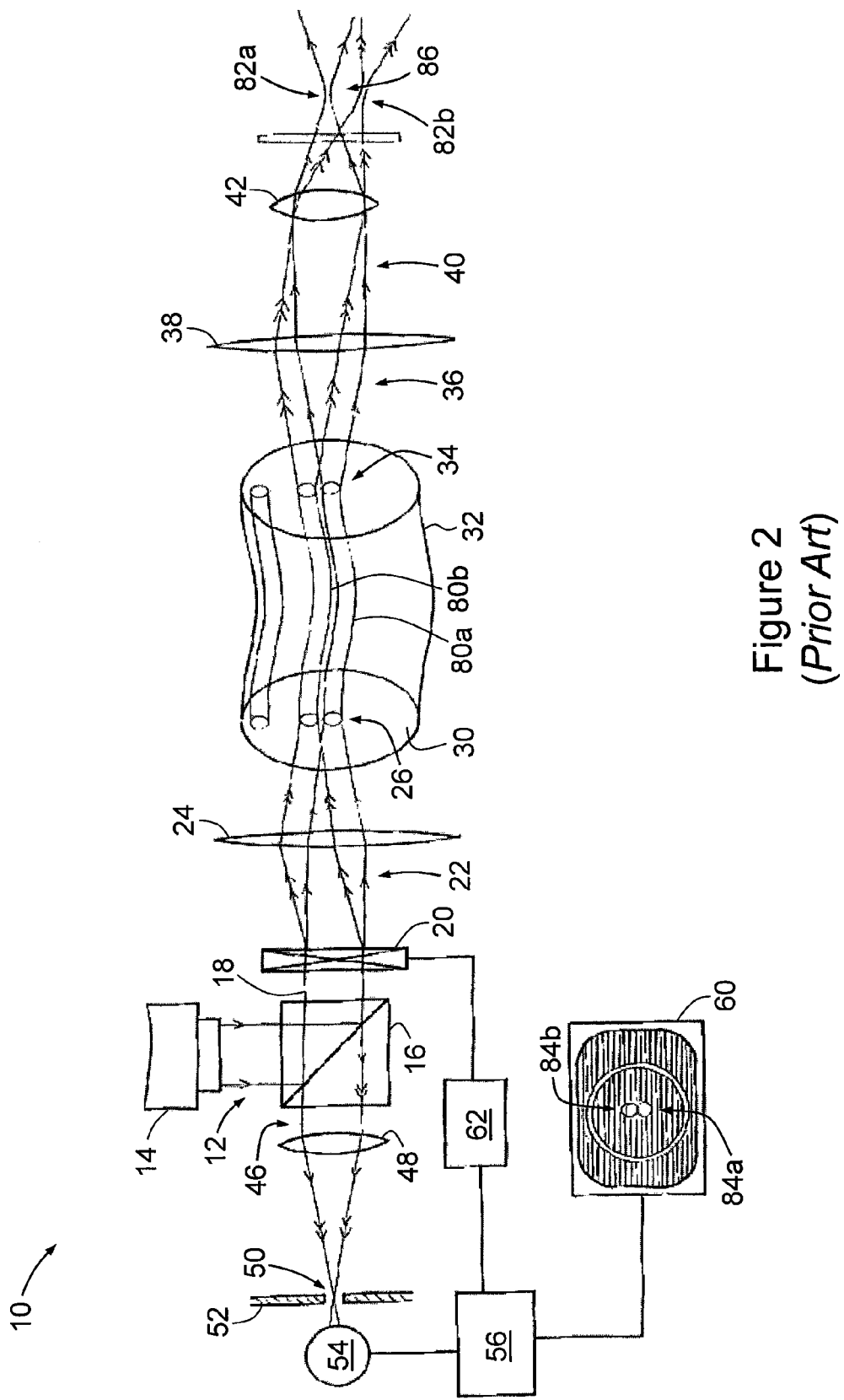
FIG. 2 is another schematic view of the background art system of FIG. 1 illustrating under-sampling.
Figure 3:
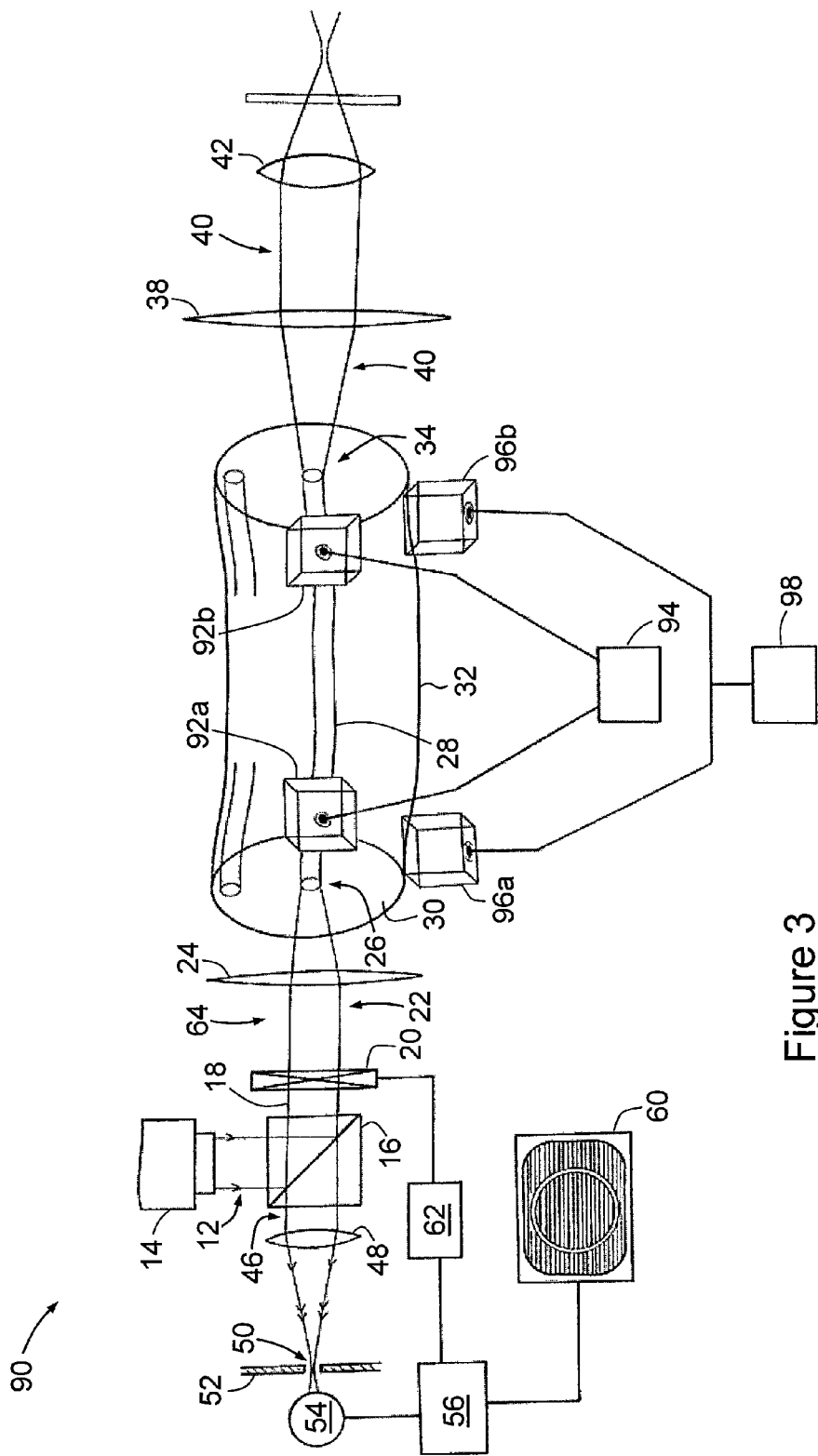
FIG. 3 is a schematic view illustrating a background art method for removing under-sampling by simultaneously dithering proximal and distal tips of a fiber bundle.
Figure 4A:
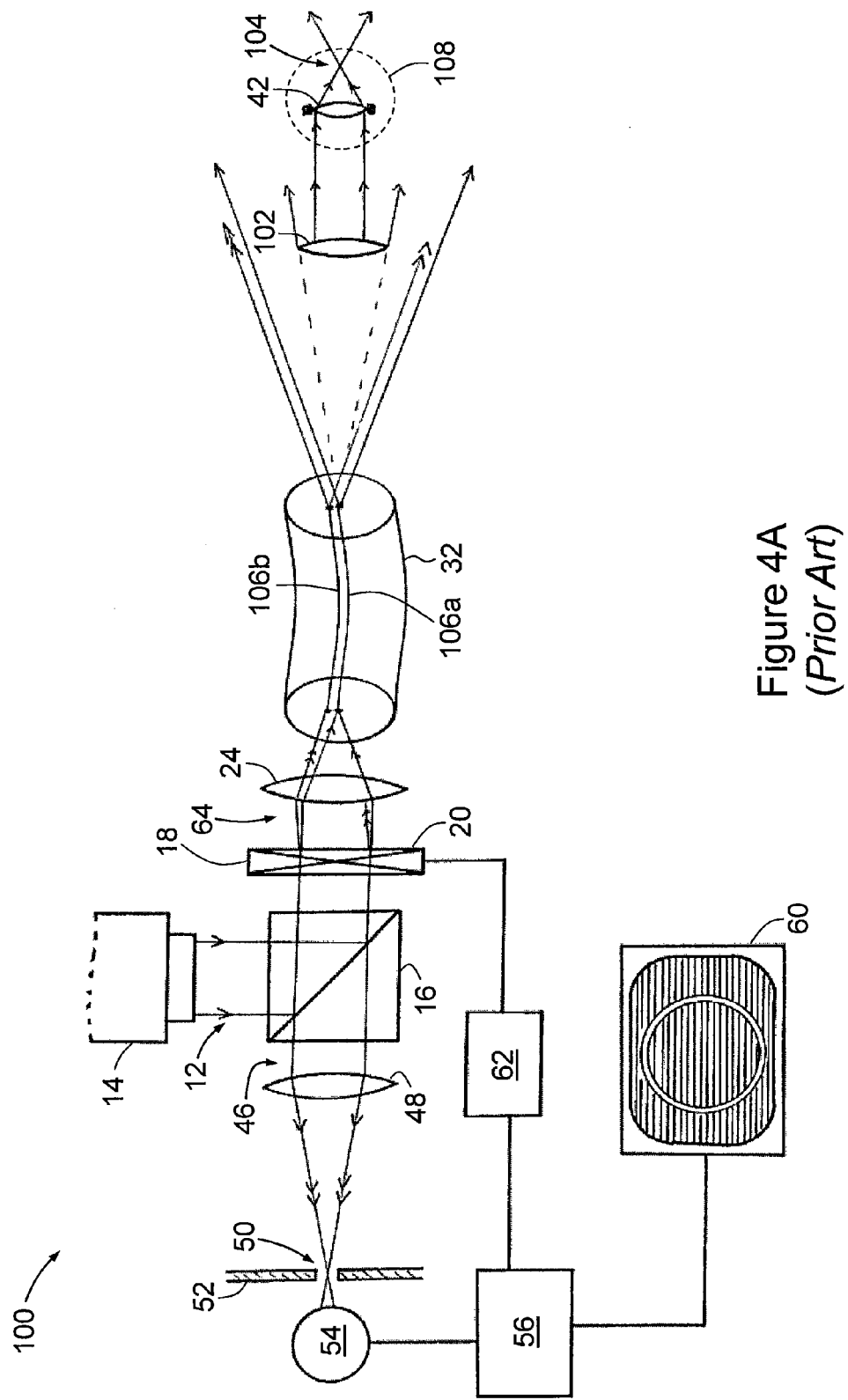
FIG. 4A is a schematic view of a prior art system in which the distal lens is highly overfilled.
Figure 4B:
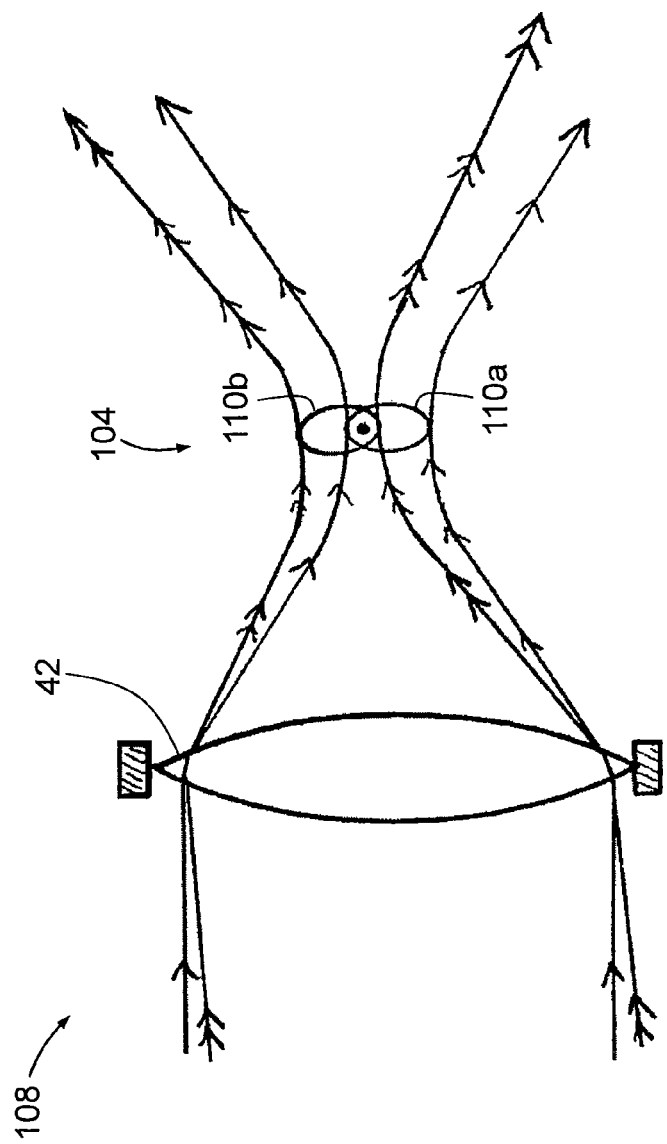
FIG. 4B is an enlarged view of the Gaussian waists region of the prior art system of FIG. 4A.
Figure 5:
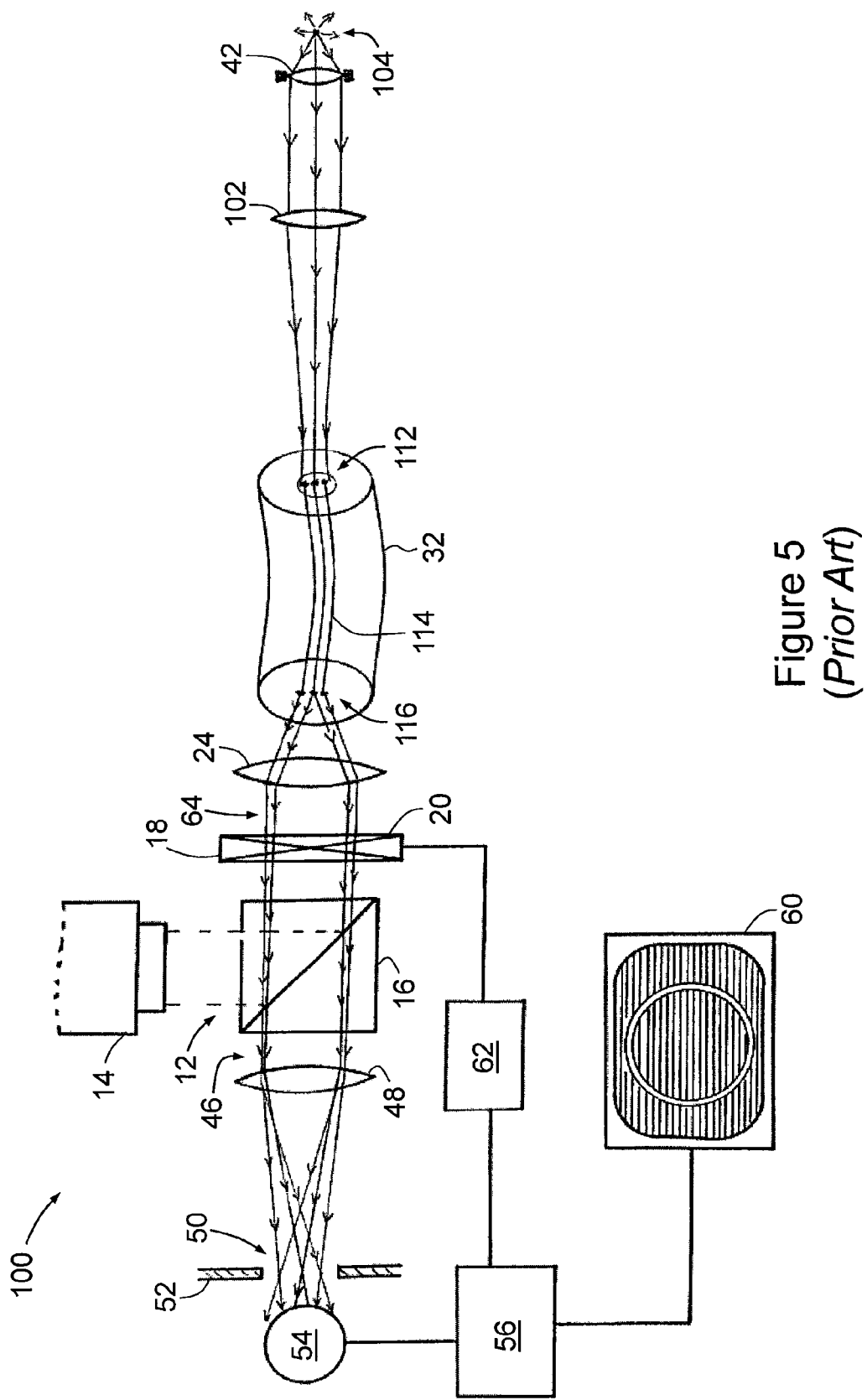
FIG. 5 is another schematic view of the prior art system of FIG. 4A.
Figure 6:
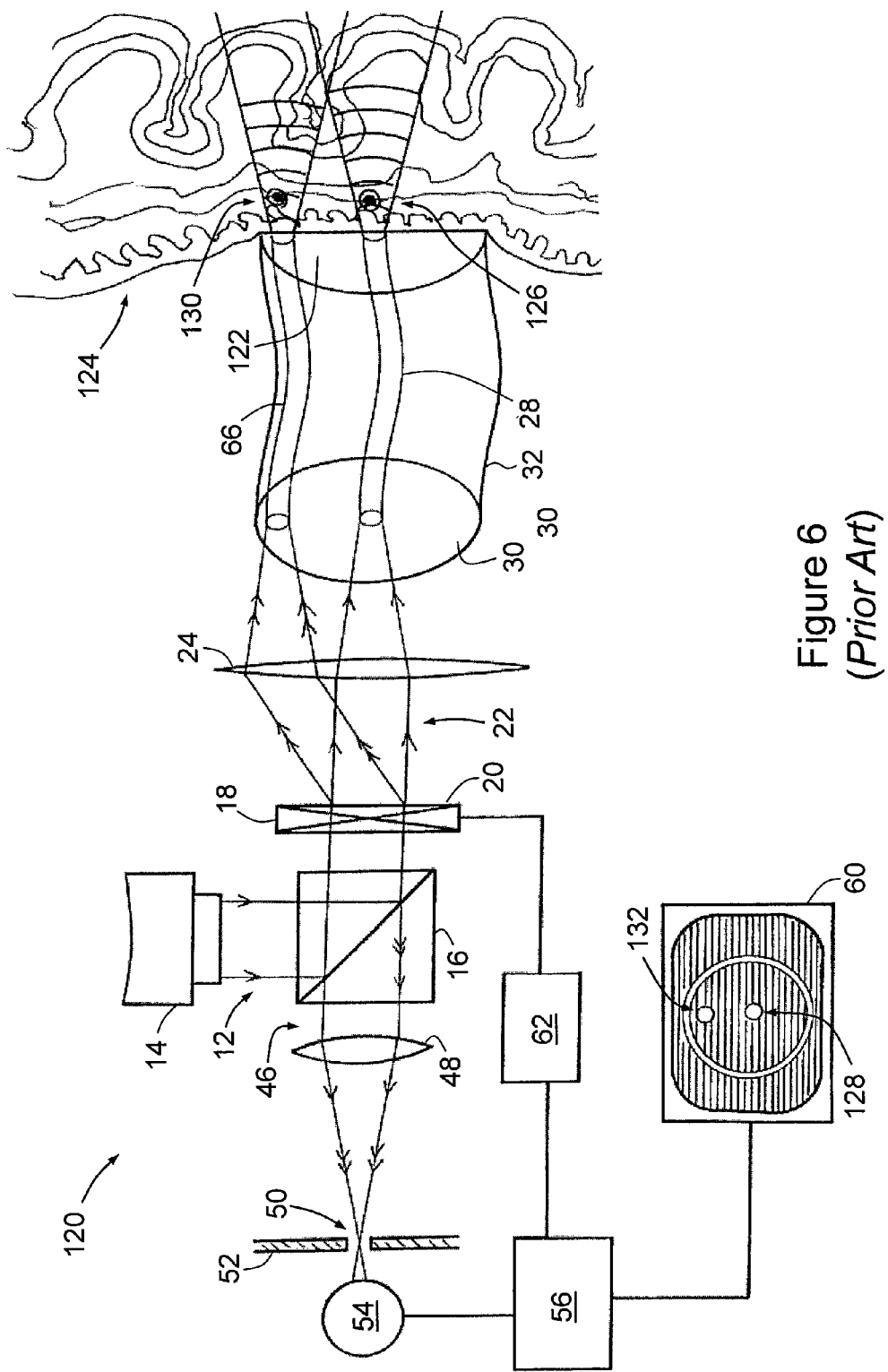
FIG. 6 is a schematic view of a contact microscopy system of a background art system, in which the bundle tip is made to directly touch a tissue to be imaged.
Figure 7:
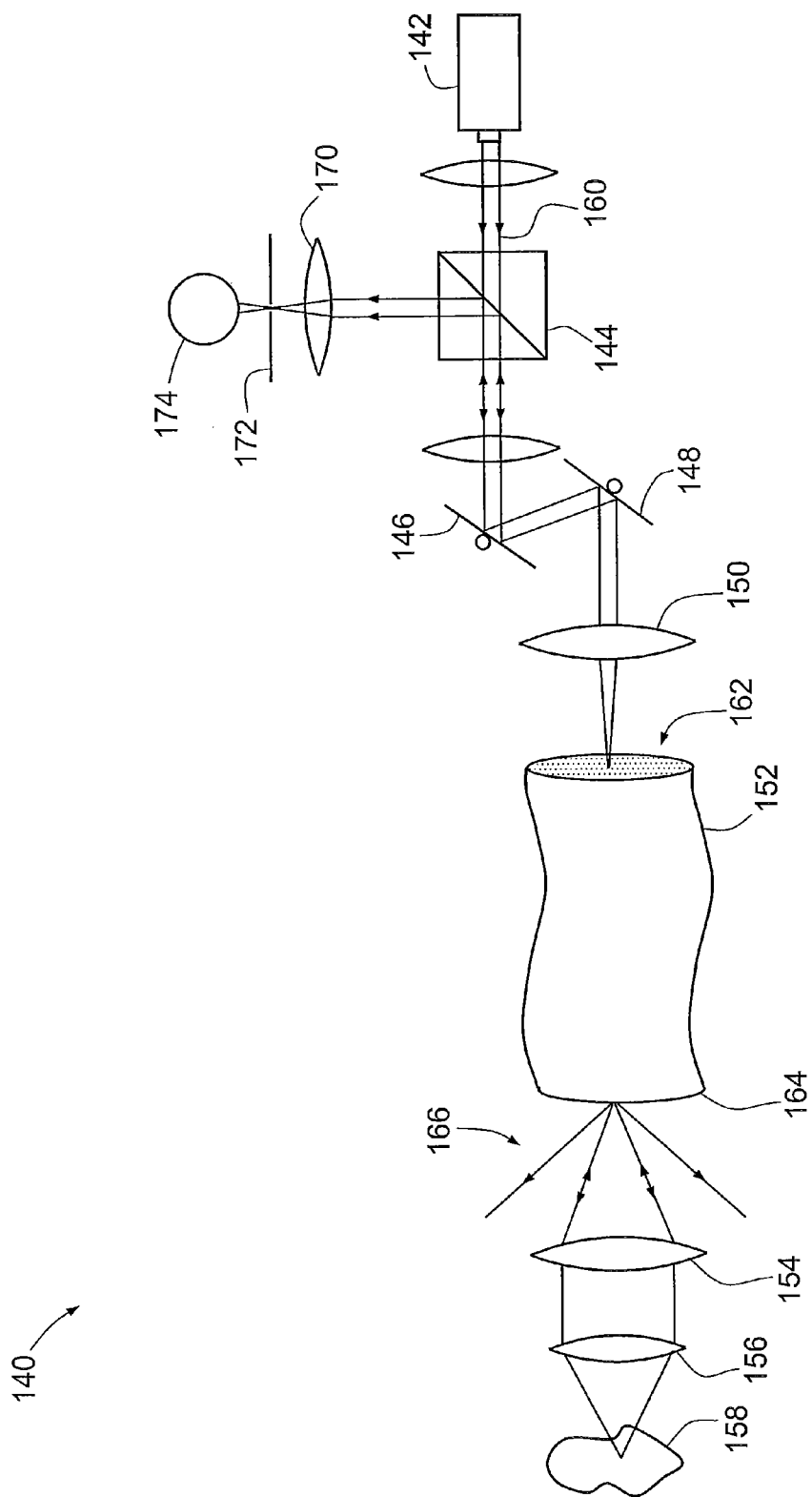
FIG. 7 is a schematic view of a fiber bundle confocal endomicroscope according to an embodiment of the present invention.
Figure 11:
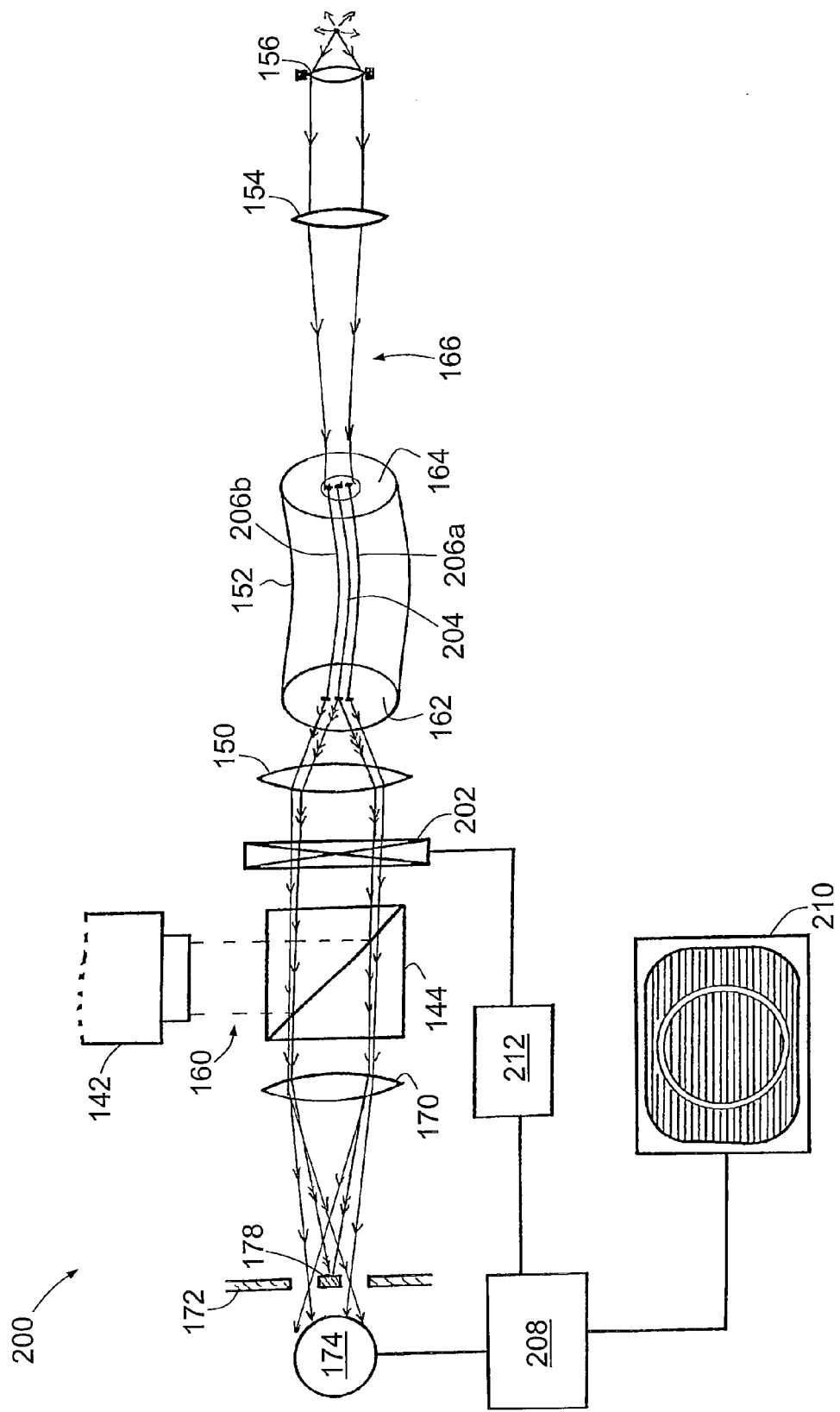
FIG. 11 is a schematic view of a fiber bundle confocal endomicroscope according to another embodiment of the present invention.

FIG. 11 is a schematic view of a fiber bundle confocal endomicroscope 200 according to another embodiment of the present invention. Endomicroscope 200 is similar to endomicroscope 140 of FIG. 7, and like reference numerals have been used to identify like features. However, rather than x and y scanning mirrors 146, 148, endomicroscope 200 includes a x-y beam-scanner 202 for performing x-y scanning. In practice beam-scanner 202 can be in the form of any suitable scanning mechanism that can provide x and y scanning, including (for example) a pair of mirrors comparable to x and y scanning mirrors 146, 148 of FIG. 7.

Occlusion or stop 178 is located at a position where it intercepts light returning from the central (light delivery) fiber 204 at any time, but aperture 172 passes return light transmitted by the six fibers adjacent to the delivery fiber (e.g. fibers 206a and 206b). This allows the majority of the signal light to return but eliminates almost all the Raman, Raleigh and Fresnel noise.

The return light passed by aperture 172 is detected by photomultiplier 174, which generates an electrical signal. This signal is fed into a bitmap in a frame-store 208 and is displayed as a point on the screen of a monitor 210. Scan generator 212 shifts the x-y beam-scanner 202 and hence the beam to a new path so that the light travels through a different fiber, illuminating another portion of the specimen at a different Gaussian waist. This portion is also displayed on the screen of monitor 210. The scan generator 212 provides an output signal to frame-store 208 so that frame-store 208 can assign the correct instantaneous x and y coordinates to the signal received from photomultiplier 174. Ultimately endomicroscope 200 builds up a final image on the screen.

Figure 12:
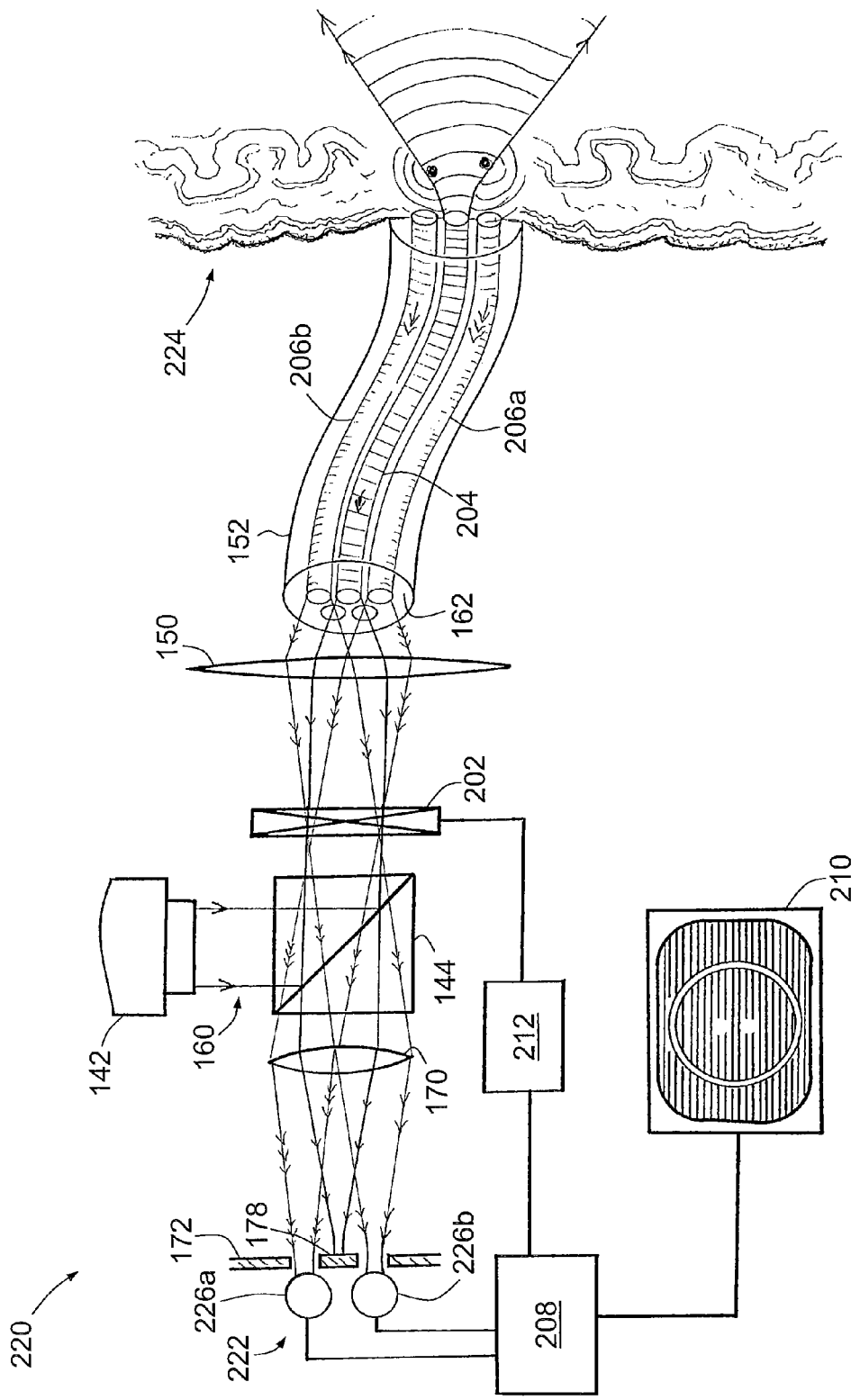
FIG. 12 is a schematic view of a fiber bundle confocal microscope for contact bundle microscopy according to a further embodiment of the present invention.

FIG. 12 is a schematic view of a fiber bundle confocal microscope 220 (which, like all the other described embodiments of the invention, may be used as an endomicroscope) for contact bundle microscopy according to a further embodiment of the present invention. Microscope 220 is similar to endomicroscope 200 of FIG. 11, and like reference numerals have been used to identify like features; being for contact microscopy, however, microscope 220 omits any distal lenses (cf. lenses 154 and 156 in FIG. 11). Further, instead of employing a single photomultiplier (cf. photomultiplier 174 of FIG. 11) to detect return light, microscope 220 includes six photodetectors 222 arranged hexagonally and located optically after aperture 172. (In the figure, a representative pair of these photodetectors 222—being those in the plane of the figure—are shown.)

Each of the photodetectors 222 corresponds to and feeds into a separate position in the image in the bitmap frame-store 208. The elimination of light from the central area minimises Raman, Raleigh and Fresnel noise and allows imaging deeper into the tissue 224. Furthermore, the relative spatial relationships between each of the proximal and distal ends of each of the fibers of fiber bundle 152 are preserved, so there is a one-to-one relationship between the six photodetectors 222 (e.g. photodetectors 226a, 226b) and the six fibers (e.g. fibers 206a, 206b) surrounding the delivery fiber 204.

Each of the photodetectors 222 corresponds to and feeds into a separate position in the image in the bitmap frame-store 208, ultimately for display on the screen of monitor 210.

Figure 13:
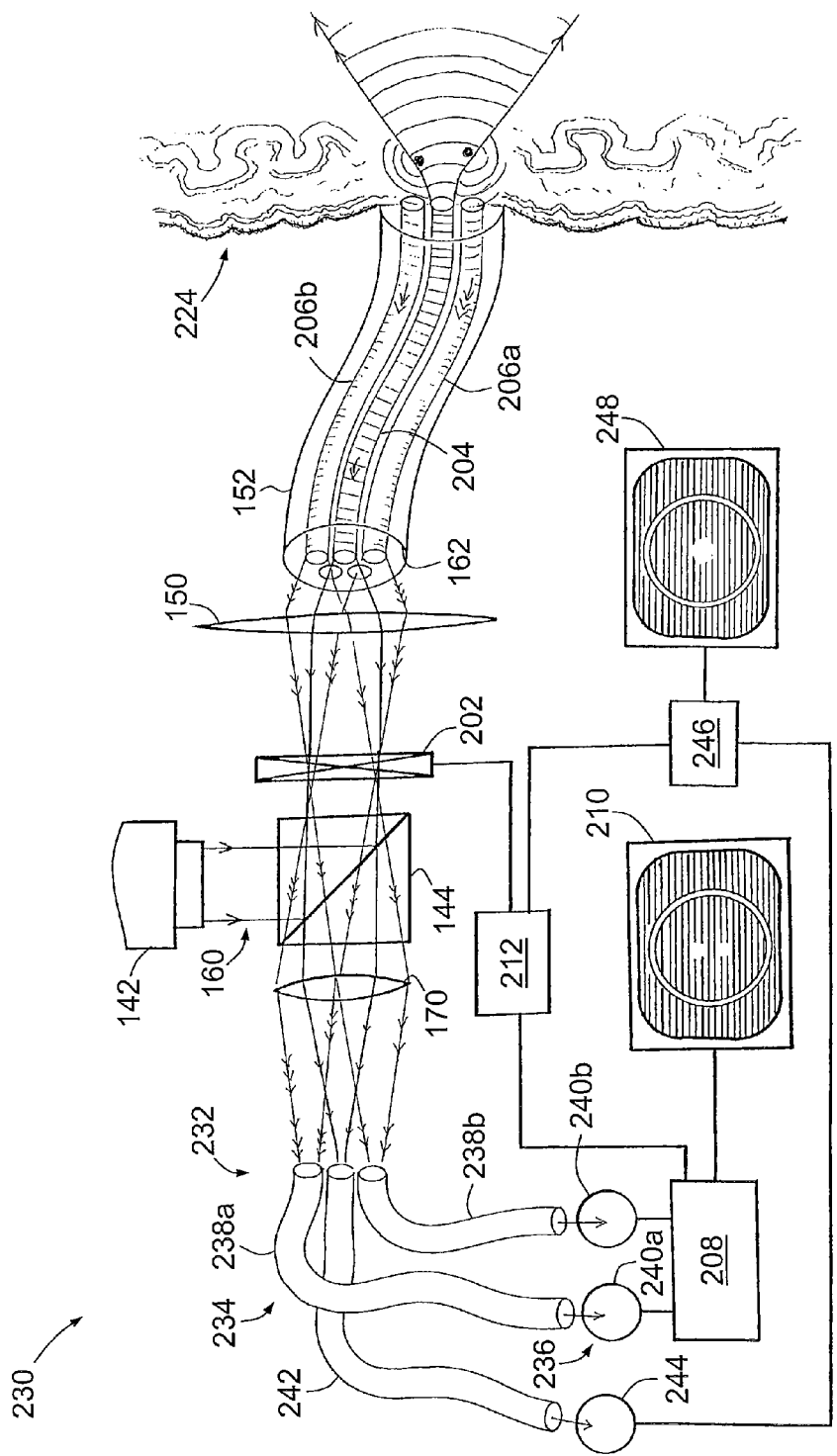
FIG. 13 is a schematic view of a fiber bundle confocal microscope for contact bundle microscopy according to a still another embodiment of the present invention.

FIG. 13 is a schematic view of a fiber bundle confocal microscope 230 for contact bundle microscopy according to a still another embodiment of the present invention. Microscope 230 is similar to microscope 220 of FIG. 12, and like reference numerals have been used to identify like features. However, microscope 230 does not include an annular spatial filter (cf. aperture 172 of FIG. 12). Instead, microscope 230 tips has a spatial filter defined by the entry tips 232 of six large gradient index multimode optic fibers 234 arranged hexagonally. These optic fibers 234 are located to collect the return light and transmit it to photodetectors 236. In this figure, for clarity only two of the optic fibers 234 are shown (at 238a, 238b), being those in the plane of the figure, and only their corresponding two photodetectors 240a and 240b are shown.

Each of the photodetectors 236 corresponds to and feeds into a separate position in the image in the bitmap frame-store 208. As with microscope 220 of FIG. 12, there is a one-to-one relationship between the six photodetectors 236 (e.g. photodetectors 240a, 240b) and the six fibers 234 (e.g. fibers 238a, 238b) surrounding the delivery fiber 204. Each of the six photodetectors 236 corresponds to and feeds into a separate position in the image in the bitmap frame-store 208, ultimately for display on the screen of monitor 210.

Microscope 230 also has a central fiber 242 to collect return light from the delivery fiber 204; this return light may be used to give a near field image in a separate channel and display screen. Hence, central fiber 242 transmits this light to a separate photodetector 244 coupled to a separate frame-store 246 for display on the screen of a separate monitor 248 (though in some embodiments the output of frame-store 246 may be displayed on the screen of monitor 210).

Figure 14:
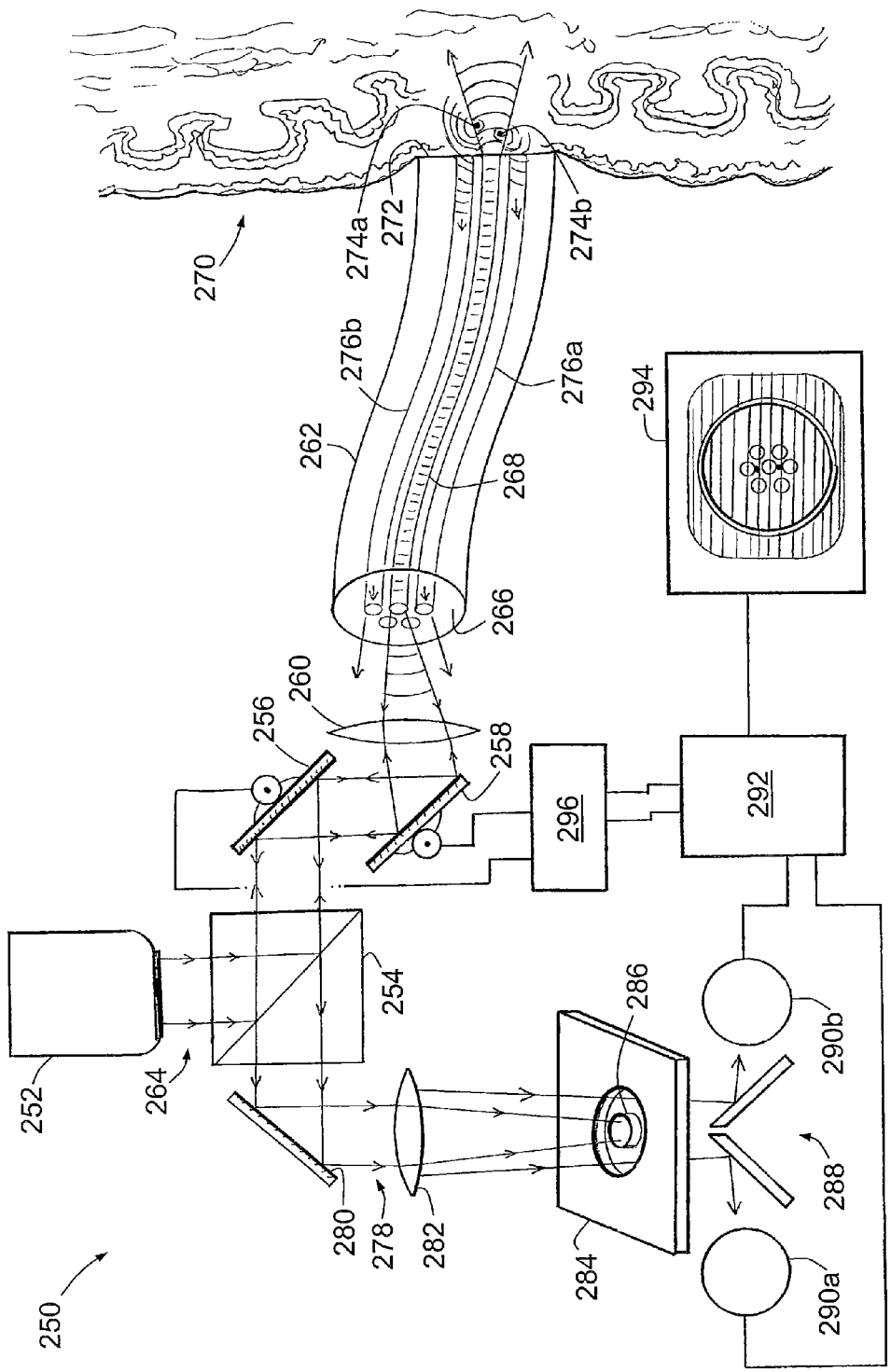
FIG. 14 is a schematic view of a fiber bundle confocal microscope for contact bundle microscopy according to another embodiment of the present invention.

FIG. 14 is a schematic view of a fiber bundle confocal microscope 250 for contact bundle microscopy according to another embodiment of the present invention. Microscope 250 comprises a TEM00 laser source 252, a beam splitter 254, x and y scanning mirrors 256, 258, a field lens 260 and a fiber bundle 262.

In use, the laser source 252 emits a beam of light 264 which passes through beam splitter 254 onto the x and y scanning mirrors 256, 258 and to the field lens 260. The field lens 260 focuses the beam onto the proximal polished face 266 of the fiber optic bundle 262. Field lens 260 is chosen so as to project a Gaussian waist spot into the core of a single delivery fiber (e.g. fiber 268) of the bundle 262 at any one time.

On reaching the distal end of the core of the delivery fiber, the light energy leaves the bundle 262 and enters the specimen 270 to be examined (which is in contact with the polished bundle tip 272). Portions 274a, 274b of the specimen 270 nearby reflect (i.e. backscatter) the light or cause fluorescence, and some of this re-emitted light returns to the fiber bundle tip 272 and is conveyed back along the delivery fiber (e.g. 268) and other fibers adjacent to the delivery fiber, but only return light that enters the six fibers (e.g. 276a, 276b) immediately adjacent to the delivery fiber is employed in forming an image. The return light in these six adjacent fibers retraces the original optical path, is converged by lens 260 and de-scanned by scanning mirrors 258, 256. A portion of this light 278 passes back through the beam-splitter 254 (following the path not traversed by the excitation laser beam 264). This light is then reflected by a mirror 280, passes through a condensing lens 282 that brings the light to a focus as an image of the core of the delivery fiber and of the cores of the six surrounding fibers at an annular spatial filter 284 (similar to aperture 172 of FIG. 8). Filter 284 is arranged to have a central blocking area or occlusion 286 that occludes and absorbs the light that forms the image of the central delivery fiber (e.g. 268) but to pass the light from the cores of the six surrounding fibers (e.g. 276a, 276b). The width of the annular opening in filter 284 is such that filter 284 blocks the light from the central delivery fiber and only allows light from the immediately surrounding fibers to pass.

The return light that passes through the filter 284 is reflected from six small mirrors 288 (or which two are shown in the figure for illustrative purposes) arranged in a hexagonal array behind filter 284; the light is reflected laterally onto six corresponding photodetectors (of which two are shown at 290a and 290b). The signal from each of these photodetectors is fed to a computer 292 and stored in an x,y bitmap for simultaneous or subsequent display on the screen of a monitor 294.

The microscope 250 also includes a scan generator 296 for controlling the x and y scanning mirrors 256, 258 and hence the beam so that the excitation light travels through successive, different delivery fibers, illuminating another portion of the specimen 270. The scan generator 296 also provides an output signal to computer 292 so that the computer 292 can assign the correct instantaneous x and y coordinates to the signal received from the six photodetectors (e.g. 286a and 286b).

Optionally, the six mirrors 288 can be located close to the filter 284 and be separated from each other sufficiently to allow light that would otherwise be blocked by the occlusion 286 to pass through a central region defined by the hexagonally arranged mirrors 288.

Figure 15:
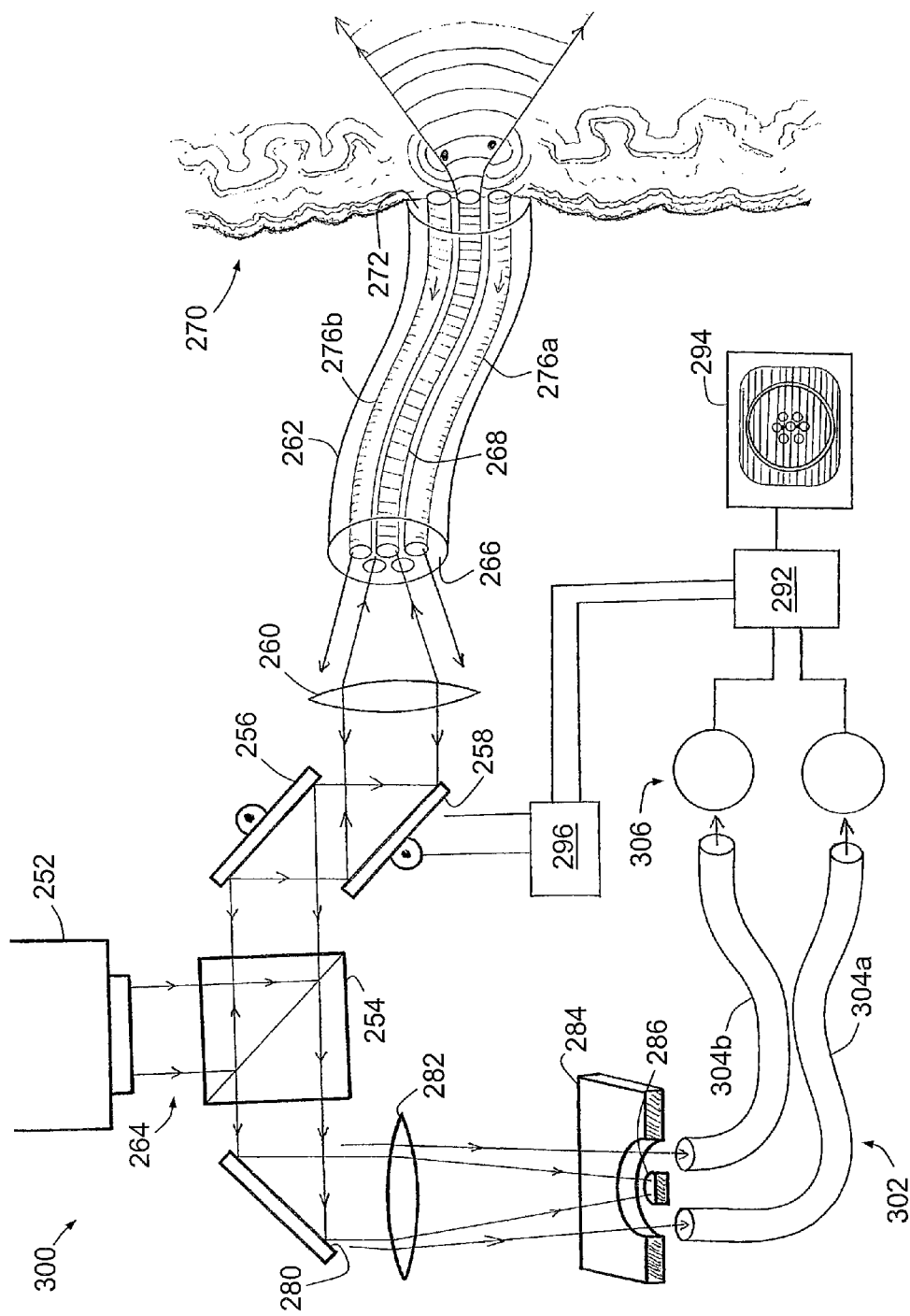
FIG. 15 is a schematic view of a fiber bundle confocal microscope for contact bundle microscopy according to yet another embodiment of the present invention.

FIG. 15 is a schematic view of a fiber bundle confocal microscope 300 for contact bundle microscopy according to another embodiment of the present invention. Microscope 300 is similar in many respects to microscope 250 of FIG. 14, and like reference numerals have been used to identify like features. However, unlike in microscope 250 of FIG. 14, return light (after being brought to a de-scanned focus by condensing lens 282) enters six large multi-mode fibers 302 arranged in a hexagonal cluster behind the filter 284 to receive light passed by the filter 284; each of these six fibers 302 (of which only two are shown for illustrative purposes, at 304a and 304b) conveys the received light to a corresponding individual photodetector 306 (of which only two are shown). The signal from each of these photodetectors 306 is conveyed to a computer 292 and stored in an x,y bitmap which allows it to be displayed on the screen of a monitor 294.

Figure 16:
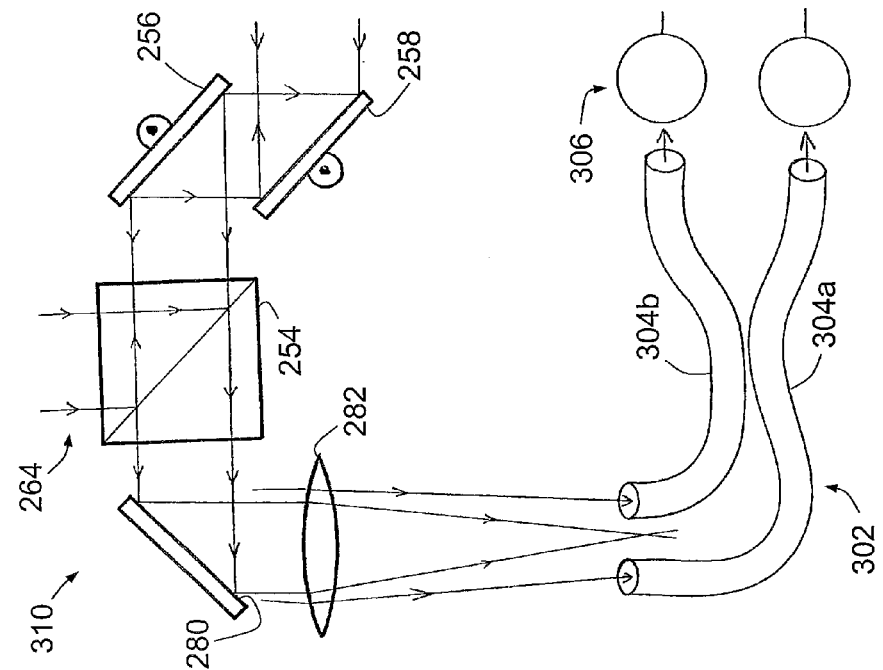
FIG. 16 is a schematic view of a fiber bundle confocal microscope for contact bundle microscopy according to another embodiment of the present invention that is a variation of the microscope of FIG. 15.

A variation of microscope 300 is shown schematically at 310 in FIG. 16 (in which features optically downstream of scanning mirrors 256, 258 have been omitted, being identical with those of microscope 300). Microscope 310 omits filter 284; instead, each of the six large core fibers 302 is positioned to correspond with a respective one of the six fibers (e.g. 276a, 276b) adjacent the delivery fiber, and to receive little or no return light from the delivery fiber. Return light from the delivery fiber simply passes between the six large core fibers 302.

Figure 17:
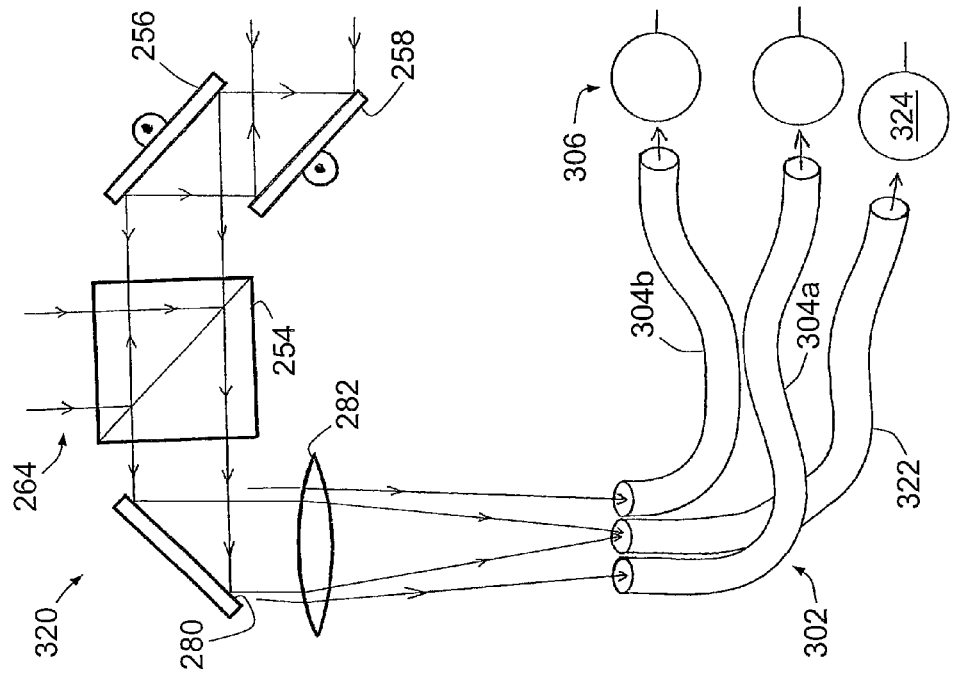
FIG. 17 is a schematic view of a fiber bundle confocal microscope for contact bundle microscopy according to another embodiment of the present invention that is another variation of the microscope of FIG. 15.

Another variation of microscope 300 is shown schematically at 320 in FIG. 17 (in which, again, features optically downstream of scanning mirrors 256, 258 have been omitted, being identical with those of microscope 300). Microscope 320 is identical with microscope 310 of FIG. 16, but additionally includes a central fiber 322 (comparable to fiber 242 of microscope 230 of FIG. 13) to collect return light from the delivery fiber. This central fiber 322 is located with its entry tip within the hexagon defined by the entry tips of the six large core fibers 302, to receive return light from the delivery fiber; this return light may be used to give a near field image in a separate channel and display screen. Hence, central fiber 322 transmits this light to a separate photodetector 324, whose output is stored in a separate x,y bitmap in computer 292 for display on the screen of monitor 294.

Figure 18:
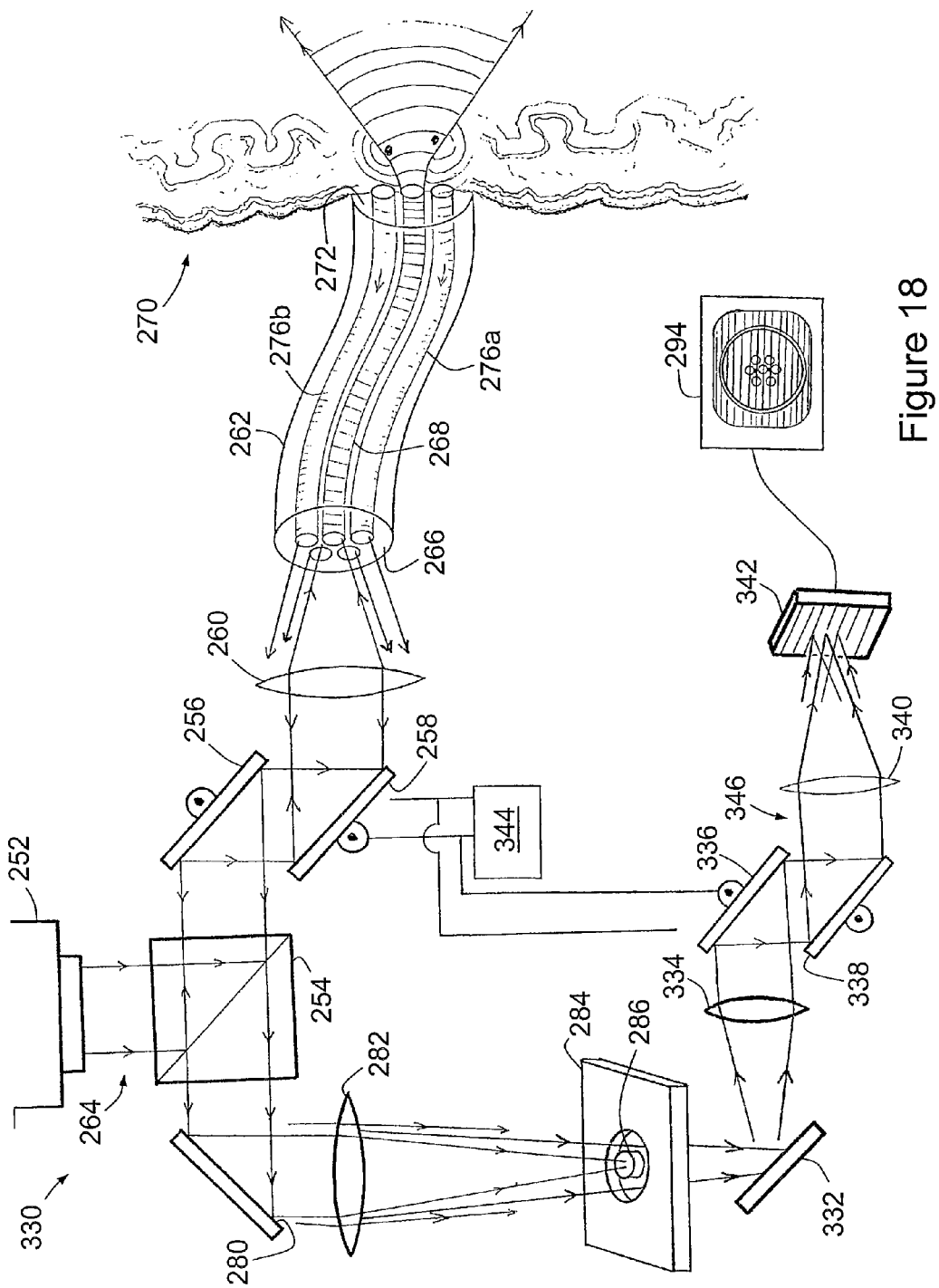
FIG. 18 is a schematic view of a fiber bundle confocal microscope for contact bundle microscopy according to yet another embodiment of the present invention.

FIG. 18 is a schematic view of a fiber bundle confocal microscope 330 for contact bundle microscopy according to another embodiment of the present invention. Microscope 330 is similar in many respects to microscope 250 of FIG. 14, and like reference numerals have been used to identify like features. However, that portion of the return used to form an image, after passing through annular aperture 284, is re-scanned and falls on a CCD or CMOS array to produce a signal that is displayed on a monitor screen.

In detail, the microscope 330 includes (optically after annular aperture 284) a plane mirror 332, a converging lens 334, x and y scanning mirrors 336 and 338, a further lens 340 and a CCD camera chip 342. Thus, the light that is passed by the annular aperture 284 (from the six fibers adjacent the delivery fiber) is reflected off mirror 332, through converging lens 334 and onto x and y scanning mirrors 336, 338. These mirrors 336, 338 are scanned in exact synchrony with x and y scanning mirrors 256, 258 (using the same power supply 344).

This rescanned beam 346 is passed through further lens 340 that maps the return light to reconstitute the relative positions of the reflective/fluorescent objects (i.e. portions of the specimen 270) from the bundle tip 272 on the surface of CCD camera chip 342. The output of the CCD CMOS chip 342 is displayed on the screen of monitor 294.

Figure 19:
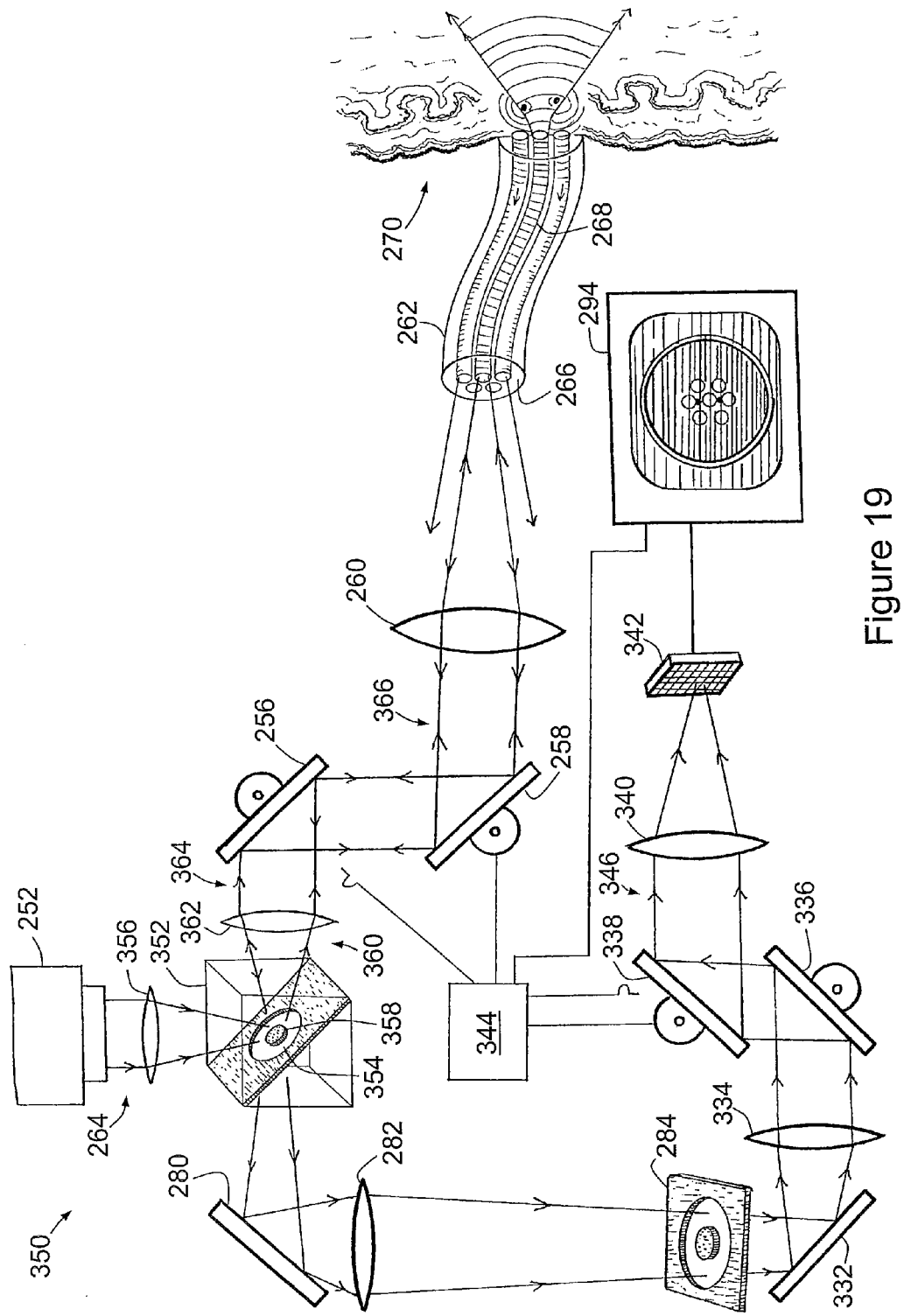
FIG. 19 is a schematic view of a fiber bundle confocal microscope for contact bundle microscopy according to another embodiment of the present invention.

FIG. 19 is a schematic view of a fiber bundle confocal microscope 350 for contact bundle microscopy according to another embodiment of the present invention. Microscope 350 is similar in many respects to microscope 330 of FIG. 18, and like reference numerals have been used to identify like features. However, rather than using a beam-splitter (with simple, planar partial mirror) like that used in microscope 330, microscope 350 includes a beam-splitter 352 that also acts as the spatial filter. The beam-splitter/spatial filter 352 has an annular aperture 354 but otherwise consists of a thin sheet of a reflective substance (e.g. Al, Ag) that is completely opaque except for the annular aperture 354. The annular aperture 284 of microscope 330 may be retained to reduce stray light, but in microscope 350 it is not essential. This configuration is expected to have an optical efficiency 400% that of the embodiments described above (owing to the use of complete rather than partial beam-splitter silvering), and beam-splitter 352 of this embodiment can be used in any of the above-described embodiments in which the return light transmitted by the delivery fiber is discarded.

In detail, a light beam 256 from laser 252 passes through a lens 356 and is focussed onto a central mirrored section 358 (surrounded by an annular aperture 354) of beam-splitter/ spatial filter 352. The reflected beam 360 from this central mirrored spot 358 diverges to a convex lens 362 which forms a collimated light beam 364 directed onto x and y scanning mirrors 256, 258. The scanned beam 366 is focussed by lens 260 onto the proximal end of fiber bundle 262 and passes down the core of one of the fibers (termed, instantaneously, the delivery fiber). On reaching the distal end of the delivery fiber, the light energy leaves the bundle 262 and enters the tissue to be examined 270 that is in contact with the bundle tip. Portions of the specimen nearby reflect the light or cause fluorescence and some of this re-emitted light returns to the polished fiber tip and is conveyed back along the delivery fiber as well as along the fibers adjacent to the delivery fiber; the light is conveyed back along the bundle 262, emerges from its proximal end 266, is converged by lens 260 and de-scanned by the scanning mirrors 256, 258.

Light returning from the central delivery fiber (268 in the illustrated example) is deflected by the central spot 358 of the beam-splitter/spatial filter 352, while light from the cores of the six adjacent fibers passes through the annular aperture 354. Light from other cores still more remote from the delivery fiber is also rejected by the outer part of the beam-splitter/spatial filter 352.

The light passed by the beam-splitter/spatial filter 352 is deflected by stationary mirror 280, and refocused by lens 282 to pass through second (optional) annular spatial filter 284.

The light passed by this second annular aperture 284 is then reflected off mirror 332 and through converging lens 334 onto x and y scanning mirrors 336, 338 that are scanned in exact synchrony with scanning mirrors 256, 258 using the same power supply 344. This rescanned beam 346 is passed through lens 340 that focuses the light onto the surface of a CCD/CMOS camera chip 342. The output of the CCD/CMOS chip 342 is displayed on the screen of monitor 294.

Figure 20:
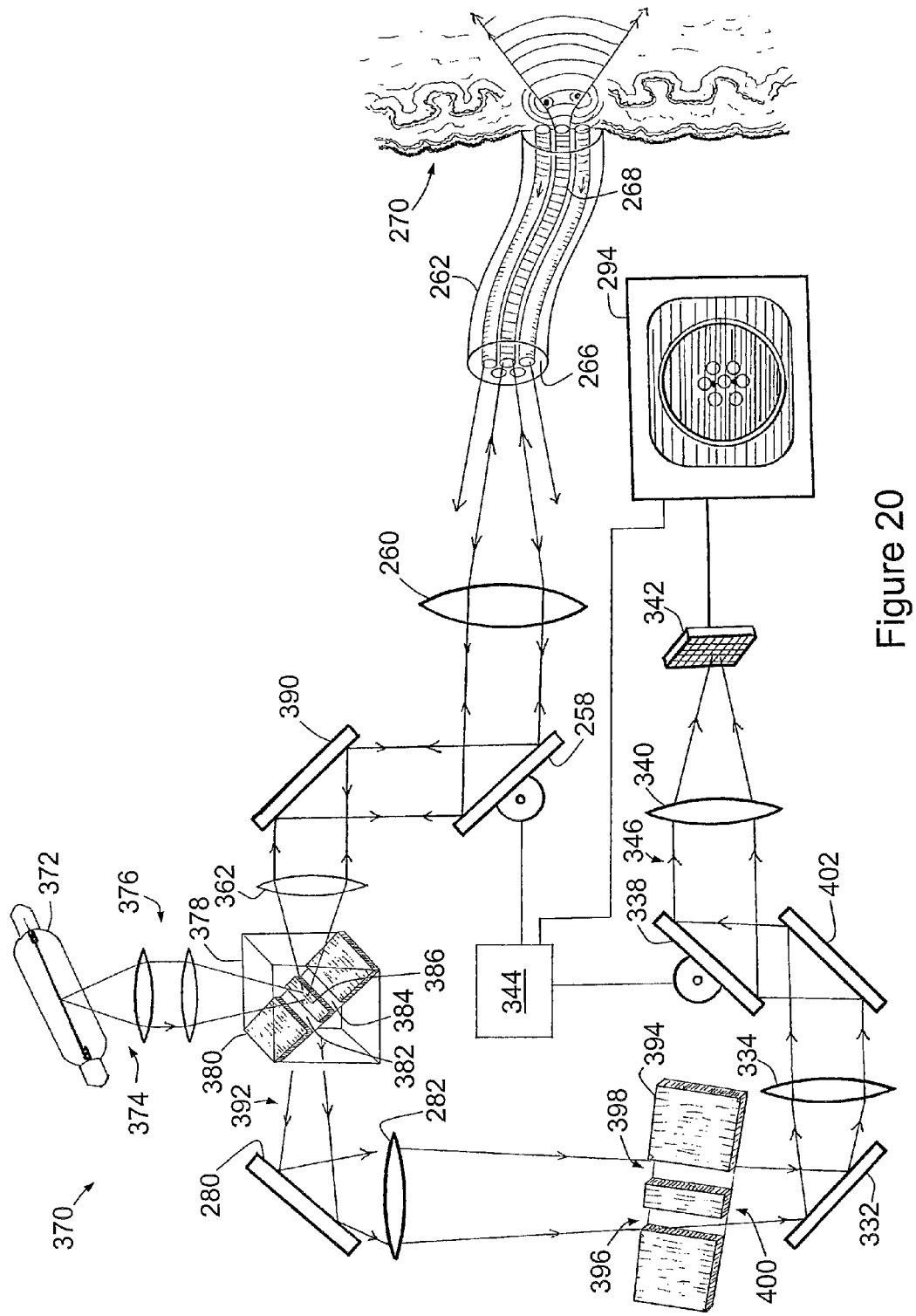
FIG. 20 is a schematic view of a fiber bundle confocal microscope for contact bundle microscopy according to still another embodiment of the present invention.

FIG. 20 is a schematic view of a fiber bundle confocal microscope 370 for contact bundle microscopy according to another embodiment of the present invention. Microscope 370 is similar to microscope 350 of FIG. 19, and like reference numerals have been used to identify like features. However, microscope 370 has a linear source of light and a beam-splitter with an elongate (rather than spot-like) central occlusion, for producing line scans in the specimen. Since a line is scanned only one mirror motor is required for each pair of scanning mirrors. That is, only one of each pair of scanning mirrors need be scanned.

In greater detail, microscope 370 includes a divergent linear light source 372 (such as a linear tungsten filament within an incandescent globe) that produces divergent light 374. Divergent light 374 is focussed to a line by a pair of cylindrical or spherical lenses 376 to impinge on a beam-splitter/spatial filter 378. Beam-splitter/spatial filter 378 comprises a mirror 380 with two narrow linear apertures 382 and 384 on each side of a thin central occluding strip 386. Apart from the two narrow linear apertures 382 and 384, the mirror 380 consists of a thin sheet of a reflective substance (e.g. Al, Ag) that is completely opaque except for apertures 382 and 384.

The line of light is thus reflected by the central occluding strip 386, intercepted by convex lens 362 that projects it via a stationary mirror 390 onto a scanning mirror 258. The beam then passes through lens 260 projecting it as a focussed line on the polished proximal surface 266 of the fiber bundle 262. The light is intercepted by those fibers in the bundle 262 that have their tips disposed along that line, and conveyed along those fibers to emerge from the tips at the distal end of the bundle 262. Reflected or fluorescent light from nearby portions of the specimen 270 is intercepted by nearby fibers within the fiber bundle, and returned to the proximal end 266 to emerge close to the excitation line of light on the end of the fiber bundle 262. This light is de-scanned and focussed as two lines on either side of the central occluding strip 386, and hence passes through the two narrow apertures 382, 384 in the mirror 380 of the beam-splitter/spatial filter 378. Other light from the proximal end 266 face tip is blocked by the outer sections of mirror 380. The light 392 passed by the beam-splitter/spatial filter 378 is reflected by stationary mirror 280 and focussed by lens 282 to an image of the proximal fiber tip cores at the plane of a secondary spatial filter 394. This secondary (optional) spatial filter 394 is essential identical with mirror 380, with a pair of elongate apertures 396, 398 and a central occluding strip 400. Light passed by secondary spatial filter 394 is reflected by stationary mirror 332, converged by lens 334, and projected by a stationary mirror 402 and scanning mirror 338 through a focussing lens 340 as an image on the surface of a CCD or CMOS chip 342. The output of CCD chip 342 is displayed on the screen of monitor 294.

Figure 21:
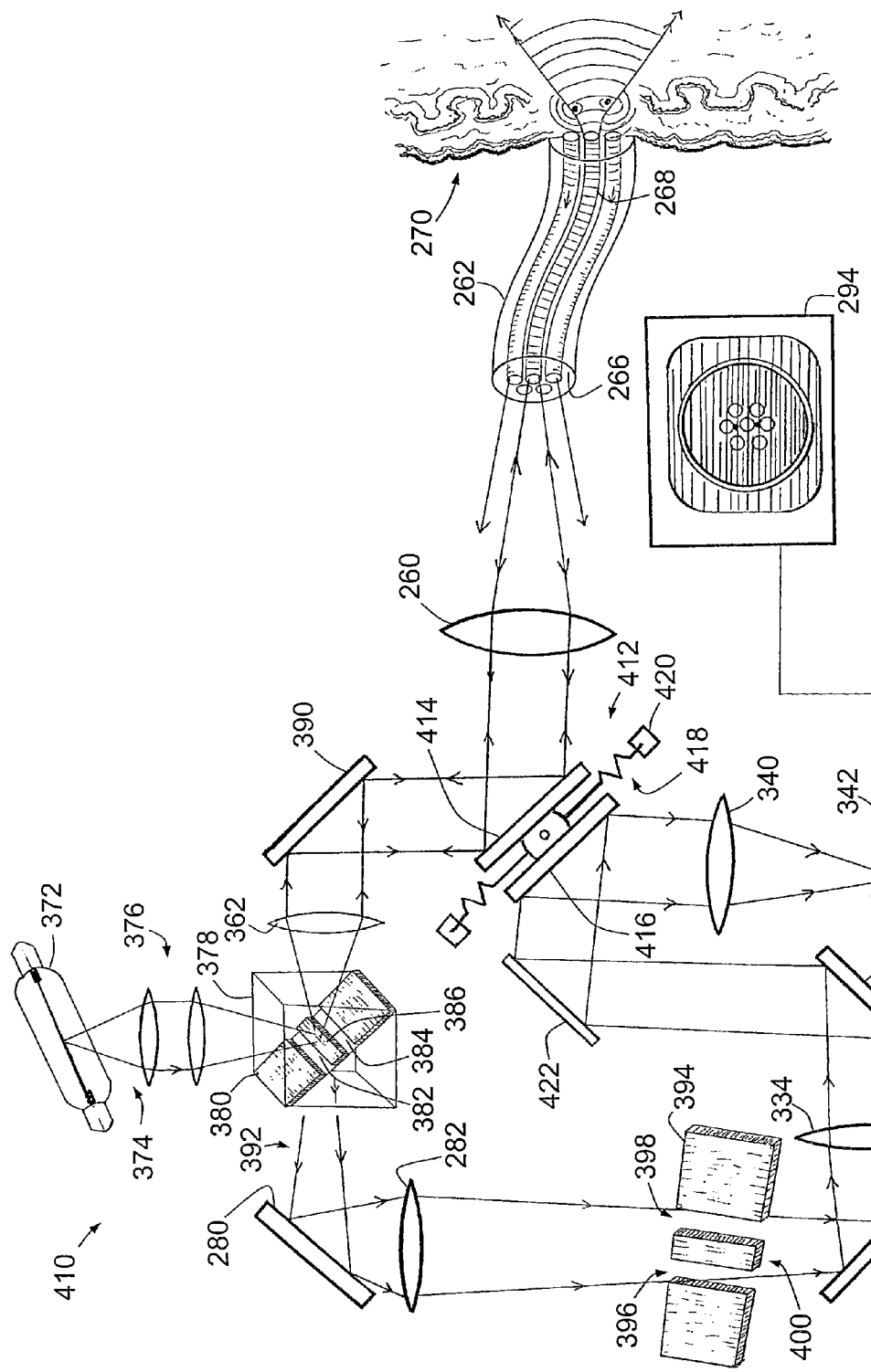
FIG. 21 is a schematic view of a fiber bundle confocal microscope for contact bundle microscopy according to a further embodiment of the present invention.

FIG. 21 is a schematic view of a fiber bundle confocal microscope 410 for contact bundle microscopy according to another embodiment of the present invention. Microscope 410 is similar to microscope 370 of FIG. 20, and like reference numerals have been used to identify like features. However, instead of two scanning mirrors (cf. scanning mirrors 258, 338 of microscope 370), microscope 410 has a double-sided scanning mirror, allowing an inexpensive system to be produced.

Thus, unlike microscope 370 of FIG. 20, microscope 410 includes a double-sided scanning mirror 412 that performs the functions of both scanning mirror 258 and scanning mirror 338. Double-sided scanning mirror 412 comprises two mirrors 414, 416 fixed to the back of each other and thereby moving synchronously with each other. A thin flexible opaque membrane 418 and surrounding frame 420 protect the CCD chip 342 from stray light.

In addition, an additional stationary mirror 422 is provided optically after mirror 402 to direct light onto the back of double-sided scanning mirror 412 (i.e. mirror 416). The use of double-sided scanning mirror 412 ensures synchrony of scanning.

The light reflected from mirror 416 is directed through focussing lens 340 (as in microscope 370) as an image on the surface of CCD chip 342. The output of CCD chip 342 is displayed on the screen of monitor 294.

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, i.e. to specify the presence of the stated features but not to preclude the presence or addition of further features in various embodiments of the invention.

Further, any reference herein to prior art is not intended to imply that such prior art forms or formed a part of the common general knowledge.

The claims defining the invention are as follows:

1. A fiber bundle confocal microscope or endoscope, comprising:
   a light source for providing a beam of light;
   a coherent fiber bundle of optical fibers that delivers said beam of light from said light source to a specimen and receives return light emitted by the specimen in response to illumination by said beam of light;

a scanner located optically between said light source and said coherent fiber bundle for receiving said beam of light from said light source and scanning said beam of light over a proximal end of said coherent fiber bundle, so that said beam of light is launched into a plurality of said fibers sequentially, at least some of said plurality of said fibers thereby acting sequentially as instantaneous delivery fibers;

a spatial filter; and a photodetector operatively associated with said spatial filter to receive said return light from one or more of said fibers;

wherein said scanner receives and scans said return light following emission of said return light from said proximal end of said coherent fiber bundle, said spatial filter receives said return light from said scanner, and said spatial filter selectively excludes a component of said return light from said photodector, said component being return light transmitted by those of said instantaneous delivery fibers that are concurrently delivering said beam of light to said specimen.

2. A microscope or endoscope as claimed in claim 1, wherein said spatial filter comprises a mechanical filter with an occlusion to selectively intercept return light transmitted by said instantaneous delivery fibers, wherein said scanner is arranged to direct said component onto said occlusion.

3. A microscope or endoscope as claimed in claim 1, wherein at least some of said plurality of fibers acts sequentially as a plurality of simultaneous instantaneous delivery fibers, and said component comprises return light transmitted by said simultaneous instantaneous delivery fibers, wherein said spatial filter is configured to selectively exclude said component of said return light from said photodetector.

4. A microscope or endoscope as claimed in claim 1, wherein said photodector comprises an entry aperture that constitutes said spatial filter.

5. A microscope or endoscope as claimed in claim 1, including a plurality of photodetectors operatively associated with said spatial filter to receive return light from one or more of said fibers.

6. A microscope or endoscope as claimed in claim 1, including one or more optical transmitters for transmitting return light to said photodetector.

7. A microscope or endoscope as claimed in claim 6, wherein said spatial filter comprises an entry of said one or more optical transmitters.

8. A microscope or endoscope as claimed in claim 1, including a beam splitter that also acts as said spatial filter.

9. A microscope or endoscope as claimed in claim 6, wherein said scanner comprises a pair of scannable mirrors.

10. A microscope or endoscope as claimed in claim 1, further comprising a second scanner for scanning an image formed by said microscope or endoscope and operable to scan synchronously with said scanner.

11. A microscope or endoscope as claimed in claim 10, wherein said scanner comprises a stationary mirror and a scannable mirror, and said second scanner comprises a stationary mirror and a scannable mirror.

12. A microscope or endoscope as claimed in claim 11, further comprising a double sided mirror with a first side comprising said scannable mirror of said scanner and a second side comprising said scannable mirror of said second scanner.

13. A microscope or endoscope as claimed in claim 1, wherein said spatial filter is located optically between said light source and said scanner, and is arranged to reflect said beam of light optically towards said scanner.

14. A fiber bundle confocal microscope or endoscope, comprising:

a laser source for providing a beam of coherent light;

a coherent fiber bundle of optical fibers that delivers said beam of coherent light from said laser source to a specimen and receives return light emitted by the specimen in response to illumination by said beam of coherent light;

a scanner located optically between said laser source and said coherent fiber bundle for receiving said beam of coherent light from said laser source and scanning said beam of coherent light over a proximal end of said coherent fiber bundle, so that said beam of coherent light is launched into a plurality of said fibers sequentially, said plurality of said fibers thereby acting sequentially as instantaneous delivery fibers;

a spatial filter defining an aperture;

a photodetector operatively associated with the spatial filter; and an occlusion operatively associated with the spatial filter;

wherein said scanner receives and scans said return light following emission of said return light from said proximal end of said coherent fiber bundle, said spatial filter receives said return light from said scanner, and said occlusion is located to selectively intercept component of said return light, said component being return light emitted at the proximal end of the bundle by those of the instantaneous delivery fibers that are concurrently delivering said beam of coherent light to said specimen, and thereby excludes said component from said photodetector.

15. A method of providing confocal microscopy or endoscopy, comprising:

launching a light beam into a coherent fiber bundle of optical fibers by scanning said light beam over a proximal end of said coherent fiber bundle, at least some of said optical fibers thereby acting sequentially as respective delivery fibers;

illuminating a specimen with light emitted by a distal end of said bundle;

collecting return light from said specimen with said coherent fiber bundle;

scanning said return light following emission of said return light by said proximal end of said bundle over a spatial filter such that a component of said return light is selectively excluded by said spatial filter from a photodetector operatively associated with said spatial filter, said component being return light-transmitted by those of said instantaneous delivery fibers that are concurrently delivering said light beam to said specimen; and detecting said return light other than said component with said photodector.

16. A method as claimed in claim 15, wherein said photodector comprises an entry aperture, said spatial filter comprising said entry aperture.

17. A method as claimed in claim 15, including transmitting said return light to said photodetector with one or more optical transmitters.

18. A method as claimed in claim 17, wherein said spatial filter comprises an entry of said one or more optical transmitters.

* * * * *